US006870046B2

(12) United States Patent
Bennett et al.

(10) Patent No.: US 6,870,046 B2
(45) Date of Patent: Mar. 22, 2005

(54) ANTISENSE MODULATION OF INTERFERON GAMMA RECEPTOR 2 EXPRESSION

(75) Inventors: C. Frank Bennett, Carlsbad, CA (US); Andrew T. Watt, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 120 days.

(21) Appl. No.: 09/843,377

(22) Filed: Apr. 26, 2001

(65) Prior Publication Data

US 2003/0176371 A1 Sep. 18, 2003

(51) Int. Cl.[7] ................................................ C07H 21/04
(52) U.S. Cl. ........................................ 536/24.5; 514/44
(58) Field of Search ............................... 536/24.5, 24.3; 514/44; 435/375, 377

(56) References Cited

U.S. PATENT DOCUMENTS 6,043,090 A * 3/2000 Monia et al. ............... 435/325

FOREIGN PATENT DOCUMENTS

WO WO 9715674 A1 * 5/1997
WO WO 9951766 A1 * 10/1999

OTHER PUBLICATIONS

Soh et al. Cell (1994) vol. 76:793–802.*

Kardassis et al., "Transactivation of the Human Apoplipoprotein CII Promoter by Orphan and Ligand–dependent Nuclear Receptors", J. Biol. Chem. 1998 273(2B):17810–17816.

Marra et al., "Interferon–γ–Mediated Activation of STAT1α Regulates Growth Factor–Induced Mitogenesis", J. Clin. Invest. 1996 98:1218–1230.

Ochiai et al., "The Role of STAT1 in Activation of IL–3–and IL–5–Induced Eosinophils by Interferon Gamma", Int Arch Allergy Immunol 2001 124:237–241.

Billiau, Interferon–gamma: biology and role in pathogenesis, *Adv. Immunol.,* 1996, 62:61–130.

Biswas et al., Interferon gamma induces the expression of human immunodeficiency virus in persistently infected promonocytic cells (U1) and redirects the production of virions to intracytoplasmic vacuoles in phorbol myristate acetate–differentiated U1 cells, *J. Exp. Med.,* 1992, 176:739–750.

Cook et al., Sublocalization of the human interferon–gamma receptor accessory factor gene and characterization of accessory factor activity by yeast artificial chromosomal fragmentation, *J Biol Chem,* 1994, 269:7013–7018.

Dorman et al., Interferon–gamma and interleukin–12 pathway defects and human disease, *Cytokine Growth Factor Rev.,* 2000, 11:321–333.

Fais et al., Interferon expression in Crohn's disease patients: increased interferon–gamma and –alpha mRNA in the intestinal lamina propria mononuclear cells, *J. Interferon Res.,* 1994, 14:235–238.

Ferrantini et al., INF–alpha 1 gene expression into a metastatic murine adenocarcinoma (TS/A) results in CDB+T Cell–mediated tumor rejection and development of antitumor immunity. Comparative studies with IFN–gamma–producing TS/A cells, *J. Immunol.,* 1994, 153:4604–4615.

Gansbacher et al., Retroviral vector–mediated gamma–interferon gene transfer into tumor cells generates potent and long lasting antitumor immunity, *Cancer Res.,* 1990, 50:7820–7825.

Novelli et al., Environmental signals influencing expression of the IFN–gamma receptor on human T cells control whether IFN–gamma promotes proliferation or apoptosis, *J. Immunol.,* 1994, 152:496–504.

Townsend et al., Unravelling the net ? cytokines and diseases, *J. Cell Sci.,* 2000, 113:3549–3550.

* cited by examiner

*Primary Examiner*—Dave Trong Nguyen
*Assistant Examiner*—Jon Eric Angell
(74) *Attorney, Agent, or Firm*—Licata & Tyrrell P.C.

(57) ABSTRACT

Antisense compounds, compositions and methods are provided for modulating the expression of Interferon gamma receptor 2. The compositions comprise antisense compounds, particularly antisense oligonucleotides, targeted to nucleic acids encoding Interferon gamma receptor 2. Methods of using these compounds for modulation of Interferon gamma receptor 2 expression and for treatment of diseases associated with expression of Interferon gamma receptor 2 are provided.

9 Claims, No Drawings

SEQUENCE LISTING

```
<160> NUMBER OF SEQ ID NOS: 89

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1

tccgtcatcg ctcctcaggg                                                   20


<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2

atgcattctg cccccaagga                                                   20


<210> SEQ ID NO 3
<211> LENGTH: 2214
<212> TYPE: DNA
<213> ORGANISM: Homo sapiens
<220> FEATURE:
<221> NAME/KEY: CDS
<222> LOCATION: (649)...(1662)

<400> SEQUENCE: 3

gttgactgga ggcggaggtt gcagtgagcc gagatcgccc cactgcactc cagcctggtg      60

actccgtctc aaaaaaaagg ggaggggggc gggggagagt tgaaagctta atatgtactt     120

tgggggctat taaagcaaac atttcgacta aaggggcgaa tcctcgaatt gtgcgatcaa     180

gcacccgaga ggagagttgg ggggggtcag gaggggtggg ggctccaggg aacgcccggg     240

ggcctgggcc ggggtctcgc ggggcccttc cggaaggatc gcggcccccg aaggtgggcg     300

tcccgcgggg ctccagtctc caggacgttc cgggaggctc cgcgctctgg gaggccggct     360

gcgtggggtc cccgcgctgc agccgcagag gccccccagg gccgcggttc ccggagcggg     420

aaagtcccgc gcgggggcgg tggcctcggg ggcgggacgg ggcgggggcg ggggcgcggg     480

cggccgagcc gaatcccctc caccgggacg ccccgctgcc gctcgggaag aggcgggccc     540

tgcgcgccct gcgctcgcca tggcggtttg ggcggcgacg tgagcggctc cgcggacccc     600

gagcggggcc ccggccgcga cctgagccgc cgccgagcgc ccggggcc atg cga ccg      657
                                                     Met Arg Pro
                                                      1

acg ctg ctg tgg tcg ctg ctg ctg ctg ctc gga gtc ttc gcc gcc gcc       705
Thr Leu Leu Trp Ser Leu Leu Leu Leu Leu Gly Val Phe Ala Ala Ala
      5                  10                  15

gcc gcg gcc ccg cca gac cct ctt tcc cag ctg ccc gct cct cag cac       753
Ala Ala Ala Pro Pro Asp Pro Leu Ser Gln Leu Pro Ala Pro Gln His
 20                  25                  30                  35

ccg aag att cgc ctg tac aac gca gag cag gtc ctg agt tgg gag cca       801
Pro Lys Ile Arg Leu Tyr Asn Ala Glu Gln Val Leu Ser Trp Glu Pro
                 40                  45                  50
```

-continued

```
gtg gcc ctg agc aat agc acg agg cct gtt gtc tac cga gtg cag ttt      849
Val Ala Leu Ser Asn Ser Thr Arg Pro Val Val Tyr Arg Val Gln Phe
            55                  60                  65

aaa tac acc gac agt aaa tgg ttc acg gcc gac atc atg tcc ata ggg      897
Lys Tyr Thr Asp Ser Lys Trp Phe Thr Ala Asp Ile Met Ser Ile Gly
        70                  75                  80

gtg aat tgt aca cag atc aca gca aca gag tgt gac ttc act gcc gcc      945
Val Asn Cys Thr Gln Ile Thr Ala Thr Glu Cys Asp Phe Thr Ala Ala
    85                  90                  95

agt ccc tca gca ggc ttc cca atg gat ttc aat gtc act cta cgc ctt      993
Ser Pro Ser Ala Gly Phe Pro Met Asp Phe Asn Val Thr Leu Arg Leu
100                 105                 110                 115

cga gct gag ctg gga gca ctc cat tct gcc tgg gtg aca atg cct tgg     1041
Arg Ala Glu Leu Gly Ala Leu His Ser Ala Trp Val Thr Met Pro Trp
                120                 125                 130

ttt caa cac tat cgg aat gtg act gtc ggg cct cca gaa aac att gag     1089
Phe Gln His Tyr Arg Asn Val Thr Val Gly Pro Pro Glu Asn Ile Glu
            135                 140                 145

gtg acc cca gga gaa ggc tcc ctc atc atc agg ttc tcc tct ccc ttt     1137
Val Thr Pro Gly Glu Gly Ser Leu Ile Ile Arg Phe Ser Ser Pro Phe
        150                 155                 160

gac atc gct gat acc tcc acg gcc ttt ttt tgt tat tat gtc cat tac     1185
Asp Ile Ala Asp Thr Ser Thr Ala Phe Phe Cys Tyr Tyr Val His Tyr
    165                 170                 175

tgg gaa aaa gga gga atc caa cag gtc aaa ggc cct ttc aga agc aac     1233
Trp Glu Lys Gly Gly Ile Gln Gln Val Lys Gly Pro Phe Arg Ser Asn
180                 185                 190                 195

tcc att tca ttg gat aac tta aaa ccc tcc aga gtg tac tgt tta caa     1281
Ser Ile Ser Leu Asp Asn Leu Lys Pro Ser Arg Val Tyr Cys Leu Gln
                200                 205                 210

gtc cag gca caa ctg ctt tgg aac aaa agt aac atc ttt aga gtc ggg     1329
Val Gln Ala Gln Leu Leu Trp Asn Lys Ser Asn Ile Phe Arg Val Gly
            215                 220                 225

cat tta agc aac ata tct tgc tac gaa aca atg gca gat gcc tcc act     1377
His Leu Ser Asn Ile Ser Cys Tyr Glu Thr Met Ala Asp Ala Ser Thr
        230                 235                 240

gag ctt cag caa gtc atc ctg atc tcc gtg gga aca ttt tcg ttg ctg     1425
Glu Leu Gln Gln Val Ile Leu Ile Ser Val Gly Thr Phe Ser Leu Leu
    245                 250                 255

tcg gtg ctg gca gga gcc tgt ttc ttc ctg gtc ctg aaa tat aga ggc     1473
Ser Val Leu Ala Gly Ala Cys Phe Phe Leu Val Leu Lys Tyr Arg Gly
260                 265                 270                 275

ctg att aaa tac tgg ttt cac act cca cca agc atc cca tta cag ata     1521
Leu Ile Lys Tyr Trp Phe His Thr Pro Pro Ser Ile Pro Leu Gln Ile
                280                 285                 290

gaa gag tat tta aaa gac cca act cag ccc atc tta gag gcc ttg gac     1569
Glu Glu Tyr Leu Lys Asp Pro Thr Gln Pro Ile Leu Glu Ala Leu Asp
            295                 300                 305

aag gac agc tca cca aag gat gac gtc tgg gac tct gtg tcc att atc     1617
Lys Asp Ser Ser Pro Lys Asp Asp Val Trp Asp Ser Val Ser Ile Ile
        310                 315                 320

tcg ttt ccg gaa aag gag caa gaa gat gtt ctc caa acg ctt tga         1662
Ser Phe Pro Glu Lys Glu Gln Glu Asp Val Leu Gln Thr Leu
    325                 330                 335

accaaagcat gggcctagcc cactggctcc ctggaagaga tcaagccatc ggagctgcta   1722

gagttctgtc tggactttcc agagaccagt attccctttt gctgcctcta aaaggcctgt   1782

ccctgcagac atgagagaca gcaggtctca tgggggtgac aagctttttt tttttttct    1842
```

-continued

```
taaagaattt tcaaaatcaa attccagaat gattttacgg agatatccca ggaaaattaa   1902

ggcttctctt aaacactaaa aaggcatgta attgcttgtt agcaaaatgg atatgacaca   1962

tctctgatac ttttttcatt attggttggg ctgagcagtc agaagacctg gtcgtcgtct   2022

tgactttggc aaatgagccg gagccccttg ggcaggtcac acaacctgtc ccagcgaggg   2082

acactgagtg gcccttcatg tacatccatg gtgtgctggc ttaaaatgta attaatcttg   2142

taaatatact cctagtaatt taagattttg tttttaaact ggaaataaaa gattgtatag   2202

tgcatgtttt tt                                                       2214


<210> SEQ ID NO 4
<211> LENGTH: 18
<212> TYPE: DNA
<213> ORGANISM: Artificial Sequence
<220> FEATURE:
<223> OTHER INFORMATION: PCR Primer

<400> SEQUENCE: 4

cagcaggctt cccaatgg                                                   18


<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5

ggaggcccga cagtcacat                                                  19


<210> SEQ ID NO 6
<211> LENGTH: 28
<212> TYPE: DNA
<213> ORGANISM: Artificial Sequence
<220> FEATURE:
<223> OTHER INFORMATION: PCR Probe

<400> SEQUENCE: 6

tcaatgtcac tctacgcctt cgagctga                                        28


<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7

gaaggtgaag gtcggagtc                                                  19


<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8

gaagatggtg atgggatttc                                                 20


<210> SEQ ID NO 9
<211> LENGTH: 20
<212> TYPE: DNA
<213> ORGANISM: Artificial Sequence
```

<220> FEATURE:
<223> OTHER INFORMATION: PCR Probe

<400> SEQUENCE: 9
caagcttccc gttctcagcc 20

<210> SEQ ID NO 10
<211> LENGTH: 339
<212> TYPE: DNA
<213> ORGANISM: Homo sapiens
<220> FEATURE:

<400> SEQUENCE: 10
ttttagtcga aatgtttgct ttaatagccc ccaaagtaca tattaagctt tcaactctcc 60
cccgcccccc tcccctttt tttgagacgg agtcaccagg ctggagtgca gtggggcgat 120
ctcggctcac tgcaacctcc gcctccagtc aaccccattt tgaaaagggt tttaagggga 180
aggagttaga aagggcccag tgaaggagga ggtggggctc tgggggtggg gggaatggcc 240
tccgagcagg gggagggaga gacagaaact tccagcattt ctaaatggcg tggggtttgc 300
cctggagccg gcggcggtgc acgagtagga agtcctta 339

<210> SEQ ID NO 11
<211> LENGTH: 54000
<212> TYPE: DNA
<213> ORGANISM: Homo sapiens
<220> FEATURE:
<221> NAME/KEY: exon
<222> LOCATION: (514)...(1420)
<223> OTHER INFORMATION: Exon 1
<221> NAME/KEY: intron
<222> LOCATION: (1421)...(12692)
<223> OTHER INFORMATION: Intron 1
<221> NAME/KEY: exon
<222> LOCATION: (12693)...(12825)
<223> OTHER INFORMATION: Exon 2
<221> NAME/KEY: intron
<222> LOCATION: (12826)...(19284)
<223> OTHER INFORMATION: Intron 2
<221> NAME/KEY: exon
<222> LOCATION: (19285)...(19490)
<223> OTHER INFORMATION: Exon 3
<221> NAME/KEY: intron
<222> LOCATION: (19491)...(24688)
<223> OTHER INFORMATION: Intron 3
<221> NAME/KEY: exon
<222> LOCATION: (24689)...(24837)
<223> OTHER INFORMATION: Exon 4
<221> NAME/KEY: intron
<222> LOCATION: (24838)...(29981)
<223> OTHER INFORMATION: Intron 4
<221> NAME/KEY: exon
<222> LOCATION: (29982)...(30141)
<223> OTHER INFORMATION: Exon 5
<221> NAME/KEY: intron
<222> LOCATION: (30142)...(30518)
<223> OTHER INFORMATION: Intron 5
<221> NAME/KEY: exon
<222> LOCATION: (30519)...(30676)
<223> OTHER INFORMATION: Exon 6
<221> NAME/KEY: intron
<222> LOCATION: (30677)...(34632)
<223> OTHER INFORMATION: Intron 6
<221> NAME/KEY: exon
<222> LOCATION: (34633)...(35318)
<223> OTHER INFORMATION: Exon 7

<400> SEQUENCE: 11
ggctggtctc caactcctgg cctcatgtga tccgcccacc tcggcctcct aaagtgctga 60
gattacaggc gtgagccacc gcgcctggca tcagtgcata ctttttgaag tgattccaag 120

-continued

```
ttatcgcccg ctttttcgt gtaacatata aatacatctc tgtatctaga aatatccaat    180

gcataattca attgtctgcg aggtatttca tcacgtattt tcacgagcgt ggccaatttc    240

aaaatagttc tacaaagagg aaatgcaaga atgtgggaag agcaaaagaa aagctctatg    300

ttgcaaaacc catttttgct aacgtgtcca gtgggctccc gggacgacct gtttttaaat    360

tcttggtctc cctgcaccgc gtccctcctt tgctgcgcta gctttatgac gcatcttgga    420

agaacagggc agatttaaaa ccctctccca acaggcgtca aacgacatgg tgcaggctcg    480

ggctggggag cgggcctgcg gctgcccagc tgctaaagga cttcctactc gtgcaccgcc    540

gccggctcca gggcaaaccc cacgccattt agaaatgctg gaagtttctg tctctccctc    600

cccctgctcg gaggccattc cccccacccc cagagcccca cctcctcctt cactgggccc    660

tttctaactc cttcccctta aaaccctttt caaaatgggg ttgactggag gcggaggttg    720

cagtgagccg agatcgcccc actgcactcc agcctggtga ctccgtctca aaaaaaaggg    780

gagggggcg ggggagagtt gaaagcttaa tatgtacttt gggggctatt aaagcaaaca    840

tttcgactaa aggggcgaat cctcgaattg tgcgatcaag cacccgagag gagagttggg    900

gggggtcagg aggggtgggg gctccaggga aagcccgggg gtctgggccg gggtctcgcg    960

gggcccttcc ggaaggatcg cggcccccga aggtgggcgt cccgcggggc tccagtctcc   1020

aggacgttcc gggaggctcc gcgctctggg aggccggctg cgtggggtcc ccgcgctgca   1080

gccgcagagg ccccccaggg ccgcggttcc cggagcggga aagtcccgcg cgggggcggt   1140

ggcctcgggg gcgggacggg gcgggggcgg gggcgcgggc ggccgagccg aatcccctcc   1200

accgggacgc cccgctgctg ctcgggaaga ggcgggccct gcgcgccctg cgctcgccat   1260

ggcggtttgg gcggcgacgt gagcggctcc gcggaccccg agcggggccc cggccgcgac   1320

ctgagccgcc gccgagcgcc cggggccatg cgaccgacgc tgctgtggtc gctgctgctg   1380

ctgctcggag tcttcgccgc cgccgccgcg gccccgccag gtgagccggg cctgggcctc   1440

cgcggcggga cgcgggcgca gccgcagcat gtgggggctg gggactcccc ggatcgtggg   1500

gtggggggaa tctgccgggt gctcagagtg ggtgggaatc tgcggggtgc tcctggtggg   1560

tgggatatgc ggagtgctca gatcaggtgg gaacctgcgg gtgccccagg tgggggtctt   1620

gcggggtgcc cagggctaga ggggcccgct gggagcccgc agcggggctg ggatgggcgg   1680

ccaggagttc cagacaggag ctgggcagca gcaggaagac ggggggcacc cctcctggcg   1740

tcctggccgc cgggacaccc ctctccggga gaggacactc ggtgcccctc cgtgaagccg   1800

gtaacctcgg ctgcgccacc tcccccaccc gcgcgcccgc gccgggaaag ccagcgtggc   1860

cccagtctcc gaatttctcg gaatgaacaa cagcaaattg aatccagggc tccggcgggg   1920

gccgcctttg ctggccactg gttctgcagc ctggcgagac tgcgcttagt ccccgcctgg   1980

agtgcctccc gaaggcctgg ctggaagcta gactcagtcc ctttgtagta gcagcggtgg   2040

agcagggacc agcgtcttgg acgggtgacc cagactcaat tccgactttg gccgagggca   2100

tgtttgacac tgggtgtgaa atctagacag ttcccgcggt catagagatg gggcagcagc   2160

attcaggcag ggctcagaac tgtccgggtc ccatcagtgt tggggcggaa gaggaagagt   2220

gtcaactgag ccaggcattt atttatttta ttgttgtttg agacagggtg tcgctctgtc   2280

gcccaggctg gagtgcagtg ggcagcatct cagctactgc agcctccgcc tcccgtgctc   2340

aagcgatcct cccacgtcag cctcccaaga aggtggtatt attggccacg cctggccaat   2400

ttttgtattt tttgtagaga ggaggtctca ctgtgttgcc caggctgttc ttgtactcct   2460
```

-continued

```
gagctccagc aatccacccg ccttggcctc tgaaagcgct gggattacag gcttgaggca   2520
ccgtgcccag ctgagccagg cttttaaaac cggttctgtc cctacccaga gagcttctta   2580
cctggcggcc tccttaacct ctgacaccag ctgaccacgc ttatgagcca aacataaaaa   2640
ccaaaagaaa cccaggcttg gtggctcacg cctgtaatcc cagcactttg ggaggctgag   2700
gcagcatcat gaggtcagga gttcgagacc agcttgacca acatggtgaa acccccgtct   2760
gtgctaaaaa tacatagctg ggcgtggtag cgcccgcctg taatcccaac tactcaggag   2820
gccgaggcgg gagaatcact tgaacccgag agctgagatc tcaccactgc actcccgcct   2880
gggcgacaga gcaagactct gtctcagaaa aaaaaaaaaa aaaaaaagaa aaagaggaaa   2940
agaccttaat gacaaatgtg tggctagaac attcttgtgt atgtatctgc ttttgttttg   3000
ctgggttctt tcccctgggg agagtgatat cataggagtc tcgagaattt agaagattct   3060
tcccattcga agctataacc ttgtgttgtg ggtttgtttt ttctaccggc attccttgca   3120
aaggcccata agttccgtat ctccttgatc tggggtgcct tgcacttgag gaaattatta   3180
actgcttttc catgggagtc agacagatgg gttcaaatcc tgactctgct tccacttggc   3240
ttcacgtctt gagcaatctg catatgcctc ctccctaggc ctcctcctaa tgagagttga   3300
tgattgtcct agtgtgggat cagcaggcga gtgacttcat gccagagagg agtgactagt   3360
ggtgatctgt ggactgtttg tgacttacct gtgatgagtc cagaggttga aagatgtatt   3420
tagaaactat agtctgacat tgccacaaca tccagctacc tgtccatctt gttaatgatt   3480
aactttaatt gtattctaca aaagttttgg tctatgtgat atgttgcaaa ataaaaaaat   3540
tttaaaaagt gaggccaggc tcggtggctc acacctgtaa tcccagcact ttgggaggct   3600
gaggcgggcg gatcacctga ggtcaggagt tcaagaccag gctggtcaac aatgatgaaa   3660
ccccgtctct accaaaaata caaaaattag gggcgtgat ggtacacacc tgtgtcccag   3720
ctactcagga ggctgaagcc gaagaatcac ttaaactcag gaggcagagg tgcagtaagc   3780
tgagatcaca ccactgcact ccagcctggg cgacaagagc aagactctat ctcaaaaaaa   3840
caaaaacaaa caaataaaaa aactggctcc attgatcctt tgaaaagtag tagcagctgg   3900
gcacggtggc tcatgcctgt aatcccatta ctttgggagg cagaggtgag cagatcacct   3960
gaggtcagaa gttccagaga ccagtgtggc caacatgtta aaaacccctt ctttactaaa   4020
actacgaaaa ttacccgggc gtggtggttg gcgcctgtaa tcccagctac ctgggaggct   4080
gaggcaggag aatcacttga acctgggagg ggaggttgca gtgagccgaa atcatgcaac   4140
tgcactccag cctgggtgac agagcaagac tctgtctcaa aaaaagaaaa aaaaagaaaa   4200
gaaaagtagt gtagtgcttt aaactaatct ctattttgca actatttgaa cattttcaca   4260
ttaaacagct taaaaacaaa cctaatggat atcttcaaaa gaaacactct tttagtcaaa   4320
acacaaagtg aaaatattca caatgattat atggcaaatg ggtggtagaa aggttttcac   4380
actttcccat aacttaccgg tgtaattttg aaattgcttt tatggtcaga gaaaaaaaaa   4440
agtgttggaa actttttttt tttttttttg agatagtatc tctctccatc gcccaggctg   4500
cagtgcagtg gcatgatcac agctcactgc agtctcaacc tcttgggctc aagccatcca   4560
cccacctcag cctcctgagt agctgggact acacgtgcac gccatcatac ctggctaatt   4620
tttgtatttt tttgtagaga tgaggtttca ccgtgtttcc caggctggtt ttgaactcct   4680
ggggtcaaga gatccacccg cctcagcctc ccaaagtgct aggattatag atgtgaacca   4740
cccagcctgg ctccggaaac agattttttta aagggagaca tagtatctat cccttagagt   4800
tctgtaagag tagaatatgt aaaatatggg acctgtggca atttgtagcc atgagctgtt   4860
```

-continued

```
aagtagtggc cgtttgcgct agatagaaaa atgtaaccaa cagcacaagt gcagtaaatc   4920
aactgaccag ttagttacct gagtgttgag gaattaaggc ttctatttgt aattgtagca   4980
ggtgctgctg actttttcag gggattggat atgtactgtg ccacagaatt ttttatcatt   5040
atttgctgac ttgaacagcc agagcttctc atatgcttag agaccaccga gaaagacagt   5100
aagtccccag caacttaaaa accattgcat gtgaatgtcc actgggtaag ctcctgagtg   5160
ttcataatct cagcaagtga aaatatcatg tagctggaat gcttttgcca cctttataaa   5220
cgatcatgat agtaacattt attggtcaga cgagatgcca agtgctttat atacattacc   5280
tctcttaatt ttctcagcca ttctttcgaa ctaggttata tctctagttt acttcctgga   5340
aagtcaaacc tttcttgata ggaagagcca aataatctag gtcaataact tgatgtccag   5400
ttgttgttgt tgtttttgag acggagtctc gccctgatgc ccaggtggga atgcagtggc   5460
gctatctcgg ctcactgcaa cctctatctc ccaggttcaa gcgattctcc tgtctcagcc   5520
tcccaagtag ctgggactat aggcacctgc caccatgctt tgctaatttt tatattttta   5580
gtagggacgg ggtttcacca cgttggctag gctggtctcg aactcctgac ctcaagtgat   5640
ccccaccgca cccccccccg ccaacccccg ccagcctcag cctcccaaag tgttgggatt   5700
acaggcatga gctaccatgc ctggcctagt atttcttgaa gagaacaatt tcctggttat   5760
ggctgaggaa tcagaaaatg ccttttttatt tctcatctgc aaggtgatgg aggtgggatc   5820
aatgatgttc acctaattga ctttcatcat aatgtccccg cccccaatag aaagatccta   5880
aagggtcagt ccttaattat caagattaaa tgattaatgt taattatatt ttattttatt   5940
atctgtgtgt gataagtgtt aatcaaacta tgctgttaag acccaggata tcctcctatt   6000
ctttttgttt gtttgtttga tatggagttt tgctcttgtt gcccagctgg agtgcagtgg   6060
catggtcttg actcactgca acctccacct cccgggttca agtgattctc ctgcctcagc   6120
ctcccaagta actgtgatta cagtatgcac caccgcacct ggctaatttt tgtattttta   6180
gtagagacag ggtttcacca cgttggtcag gctggtctcg aactcctgac cttaagtgat   6240
ctgcctgcct caacctccca aagtgctggg attacaggca tgagccaccg cacccagccc   6300
ctcctattcc taaatatgca taaagtctga aatgcctgga tctgggatag gtagatcaaa   6360
ggtgttggga tgggtcagga aggcagagtt gttcattcac ctcttcactg gttgttaaat   6420
ggtcctagtg tttggccctg agtgtataaa aatgattaag acaatgaatg tagagaatag   6480
tctacttaga gaccttgtca gaatgtctgt attaccatgt gtactataat agatacacat   6540
acactatgtg ccatgatttt tcaaaagtgc tagaatagaa atatttttaa atgttatagg   6600
acactacttg ccaggaagag ttgaagaaag tccaatagag gaagaacaaa ctgagctggg   6660
ttttgaagca tggagtttca gattaaagaa aagaagaaaa ggccaggtgt ggtggctcac   6720
gcctgtaatc ccagcacttt gggaggccga ggcaggtgga tcactaggtc aggagttcga   6780
gaccagcctg gccaagatgg tgaaacgctg tctctactaa aaatacaaaa attagctggg   6840
cacagtggcg ggtgcctgta atcccagcta ctcaggaggc tgaggcagga gaatcgcttg   6900
aacccaggaa gtggaggtta cagtgagcct agatcgtgcc actacactct agcctgggtg   6960
acagaacaag actgtctcaa aaaaaaaaga ggccgggctc agtggctcac acctgtaatc   7020
ccagcactgt gggaggccaa ggcaggcaga tcaggaggtc aggagatcaa gaccatcctg   7080
gctaataatg gtgaaacctc gtctctccta aaagcacaaa aaaatagcca ggcgtggtag   7140
caggtgcctg taatcccagc tactcgggag gctgaggcag gagaattgct tgaacctggg   7200
```

-continued

```
aggtggaggt tgcagtaagc cgagatcacg ccactgcgac actgcactcc agcctggggg   7260

acagagtgag actctgtctc aaaagaaaaa aagaaaaagc aatatgcaaa attatgtagg   7320

tccaaaataa aataggatag agtttatggt attttagcga gtggtggtga ttggtctggg   7380

ataagatctt gaaggatttt cagcttactc aagtctgaac tctaccctcc atgccaggaa   7440

tcggcaaagt ttttctgtaa agaactagac agtatgcact cagatggtta cagaagtttg   7500

attaaatggc tgatttctga attaggtatg gcgcttgaga ctctgcctag ggagagtgct   7560

caggtcatgc ttatatgtga aaatgtgtcg ttattttttc ctcttgctct cacacatgtc   7620

ccttggtttc ctaagtgagg ttttgaaaat gaaattttga cagttgagcc aaaatgccct   7680

ctataagcac gtgtatttcc ttctttaaag aattccctct caggaattcc ctctctaatg   7740

tattgtaaga tttggggttc gaccattaac gcattagtcc agttcaataa gcttcatttt   7800

tttttgttgg tagcagggtc cattttatgg gcgaacatac cagtaagttc cttgccttcg   7860

gggaagttta agtttattaa aagcagttac agatatatta cagatgtatt atacaggagg   7920

ttctcaagag gcaagaaggt tcagcaagtt cattgtctta attacaataa tttttttttt   7980

ttttttttga gacagagtct ctctctgtca cccaagctgg agtgcagtgg tgcaatctcg   8040

gctcactgca gcctccacct cccaggttca agtaaattct ctggctcagc ctcccaagta   8100

gcttgaatta caggcaccca ccaccatgcc tggctaattt ttatattttt agtaaagatg   8160

gggtttcacc atcttggcca ggctggtctt gaactcctga cctcatgatc cacccacctt   8220

ggcctcccaa agtgctgaga ttacaggcgt gagccactgc ggccagccta caacaatttt   8280

tttttttttg agacagagtc tcgctcttgt cgcccaagct ggagtgcagt ggcgtgatct   8340

cagctcattg caacctccac tgccgggttc aaatgattct tgtgcttcag cctcccaagt   8400

agctggaaat gcaggtgtgc accactatgc ctggctaatt gttgtatttt tagtagagac   8460

ggggtttcac catgttggcc aggctggttt caaactccca aactcaggtg atccgcccac   8520

ctcagcctcc ctaagtgctg ggattacagg cgtgagccac cacgcccatc caattagaat   8580

aactttttac atgttgtatt tttaaaattc ataactcata atctaaaatt tatgctcagc   8640

acagctaact ttggagacct accaagaatg gtgcaatgat tcagcagcta ctcatggtaa   8700

gacaagagta tctgggtgta acctgtatga aacctgcatc tcacaaccac tgctccttct   8760

ccccagcctt ccagccctgg tgtttcccat cgggggccat gtggcctgga acacagaggc   8820

tgggctgccc aaggacaggc cccctggcct acaaaaagga cagtcttatc acagatgtgc   8880

aatccttggc acttccctgt ggcgtctgca gttctgagac tgattttctt ctataaatgt   8940

gaaaagatag gggatgatag gaaacccgga tataaggcag aacaatgttg cttgggccat   9000

ctcttacacc tcagtgaaac ggaaaatgaa ggaaatggaa ggctggcatg ggaaccccga   9060

cttatacagt gatgcccttt tgctgttcca cgcgtcgctt ggggtggaag cccttccttg   9120

tcccctcgcc acccaccccg gagccccttg gtgcttcctt tctgaactga atgcttagac   9180

tggggaacta gaggtgcccg gaaagggaag tcgggaagaa gagactattc ctgttggttc   9240

ctccccagag atgggagatg gtgaacaggc gtgtggaggg cggaataatg gtccccaaag   9300

atgtccacgc cctcatcctc agagtccgtg aacctgggaa tgtgctgcct gacgtacaaa   9360

agggactccg cagatgtgag taagttaaga gccctgatgt ggggagattg tcttgcattg   9420

ttgggccaag tggccttata ccaccacagg gtccccaaaa gatggagcag aggcagaagg   9480

ttcagtacca gggagacaag aaggatgcgg ccaaccttgc tggaggaagg tgccctgagc   9540

caaagaatgg gagtggcctc tagaagctgg gaaaggcaag gaaatggatt ctccctggag   9600
```

-continued

```
gctcgagaag gaccccagcc ctgctgataa cttgacttta gtcagtgaga ctgactttaa   9660
acttctgacc agcagaacta taagaaaata aatttagatg tgattttta aaatttattt   9720
atttttagag atggggggat ctcgctatgt tggccaggct agagtgcaat gattattcac   9780
aggcatgatc atagcacatg cactacagcc tcgaactcct gggctccagt gatcctcccg   9840
cctcagcccc ttgagcagct gggactacag gtgcgcacca ccacgcccag ctaaatctgg   9900
gttgtgtgga gtcactaggt tagtgataat gtgttacagt gataagaaga acctaataca   9960
ggaaataaaa ggagttgtca gattctttga atgcccaacc ctaagcagac actcaccctg  10020
ttcctggaaa gagccgggtc cagctgcgtt ttctcatggc ccaataacaa gaagcagaca  10080
aactaggaag aaagagaatt tattgctgta acaggaaggt cggagataat ccgaccagac  10140
caactcaaag tgtttgattt tctttgtgct tacataggtt tgggttatgt gcctatgtgt  10200
ggtattgcac taagtctatg agtaactaat tttgtttcaa ctagaaagtc agaggccaaa  10260
aatgtgcttt ctaagtctaa tcaagctgtg aggtccccga taccgtcaag gcctgtctcc  10320
taaattctat ttaatgagga ctgtggtacc agagcattta tttatttatt tatttttgag  10380
acggagtgcc gctctgtcgc ccaggctgga gcgcagtggt gcaatcttgg cttgctgcaa  10440
cctccgcctc ccgggttcaa gcgattctcc tgcctcagcc tcccaggtcg ctgggactac  10500
aggtgtgtgc caccatgcct ggctaatttt tctattttta gtagagacag ggtttcacca  10560
tgttggccag gctggcctcg aactcctgac ctcaggtgat ccaccacctc agcgtcccaa  10620
agtgctggga tttcaggcat gagccactgt gcccggccag gagtttattt ctatcttgtc  10680
tcatttacag tttggtccgg agagctgcct tagactctcc aataaatcta ttcaaacagc  10740
tgcctctgtt atcttgactt gctccaggtt tggaagaagc ctgtgtagga tctgtgtttc  10800
atttctggct ttgatgtctg ggcgtcagtt tccctggggt taattattag cttaatgtga  10860
aggcagcatt gtggaaattt ctctgcatag ttcggatgct attcagatct gtctgtgtga  10920
ctgtcatgca ggcctctctg tgtgactgtg agggagcatt gacctgccac cacccccctc  10980
tggaagcatc cagtccccaa ctggctttgg gcattgctag gtcatagcag ccacagcaca  11040
cctggtgggc ctgcctcttg ccacgcagct ttacctgtct gccttcggcc caggatgtca  11100
tgaggcctgc tgtgtgtcag gagaagtgtt gttagctggt tgggtgaagg tcacccagag  11160
ctcataggtg tggaggggag gggcatccta taactaaaca aatggccgca gacttggcaa  11220
ttcatctttc agaagaagag ccagtggtca ggctgtcagc tgatctcttt gaggttgagc  11280
gcatttaccg aaaatgtgtg gcttgaattt cctgctttga attttggaac agcatgtttt  11340
tcaaaccttt cttccacctt ctgggcattt cttattaatc tttttggtca aaagccttat  11400
cttgattatg ttttctttct aagacaaagg gctccctgtg aagtacctgc ttgggaaagg  11460
gaggagttgt ggcagtttct tctaggtccc cgaaggctcc ctgtgaagta cctgcttggg  11520
gaagggagag gttgtggttg tttcttccag gtcaccccaa agagagggat tctgatattg  11580
gtggtgtttc cgggggagta tattctttct ctgtttattg ccccctaacc tttttttttt  11640
tttttttttt tttggagaca gagtctctct ctgtcgccca gactggagtg caatggtgcg  11700
atctcagctc cctgcaacct ctgcctcctg ggttcaagcg attctcctgc ctcagcctcc  11760
tgagtagctg ggattacagg cgctcaccac cgcacctggc taacttttat atttttagta  11820
gagacagagt tttgccatgt tggccacact ggtctcaaac tcctgacctc gagtgatctg  11880
ccttccttgg cctcccacag tgctgggatt ataggtgtga gccactgagc tcgggccgtg  11940
```

-continued ttgtcctcta actttaatgt gtgtgagaag cagctggaaa gcttgtttaa aatgcagatt 12000
tcctgggggc ctcaggacct gcactttaac cagcacccct gtgattgcga tgctgggggt 12060
ccttgagaga cgacaactct gatggtgccc agaagtcggc gttccttgcc ctcccctgca 12120
gcttgggctt tgcgtacctg atttaggatg tttgtgtgtt tttgcgtgtg tagtgtgtgc 12180
acgtgtgcac gtatttgcgg acatttacca gacacttcct tggtactaaa tctgaaagct 12240
aacgcgtgtc acatgatcac cacgttaatc ttcgccacag ccctgtgggt gtatcattat 12300
tgacccctta ttcctgaaaa agaaaactca agctcagaca ggtgaagtga cctgccccga 12360
gcctaatgca gttactaatg gtagaactgg gaccccagtc cggccagact ccagggccca 12420
ggacctgttc gtaacaactg ggacctgcag gtggaaaggc tgccccaggc gcctcttttc 12480
tttttgtgct gcctgtacca gtagggccat ctttgtagcc aaaagtcggg ggtgtggggc 12540
catgcccagg gggacctggt aatgccattt ctgcactttg acaaaaactg agttgtatga 12600
atgacttaga taatggacat tgaaacattt ttgtaattat ttccctctct ctcctccctt 12660
cctccctctt ctttttctct gtccccctca agaccctctt tcccagctgc ccgctcctca 12720
gcacccgaag attcgcctgt acaacgcaga gcaggtcctg agttgggagc cagtggccct 12780
gagcaatagc acgaggcctg ttgtctacca agtgcagttt aaatagtaag ccggtatttc 12840
tgttggatcc ttgctgggag ctgtgggggc atcgtgcgga accctggggc cacatactag 12900
tccctgcctc tgtgcagggt ttgttatcaa acccgtggga aacacatcgt tcttggagct 12960
tgtaaaatct ctgaggacag aggtttcaca gcctccccact catctgaagg cttaaactac 13020
actggcagtc aggactccgc tgtctaacca cacgggttct tgctttggtg gaaagttcat 13080
tctttcgctg gtttcaggag aaaggttgta aaaataggct tccaccatgg aagaacagga 13140
ggcagctttt agtcttcatc ttcgggctta aaaatcggat tgatttaacc ttatagacca 13200
aatatggcct gatcagaaat ttgtttggtt aattacaatg aattctgagt ttctcaactg 13260
gttttccatt ttgcatatta tcctggctct ttcatctgtc tcttgcctct tcaagctttt 13320
gcagaattgg ccatcacttg atttgcaata taaatacata tagaaagagg gcaaagtcca 13380
catcctttgt tattttttgt ttacgttgtt aagtaggtta attgaagagt aaggtgaagt 13440
tattggctaa gtcattttgt actatttggt aaaccaaatg taaagacatg atgatgtcca 13500
gtgcttgtga gatgggactg gttcatatgt gttcacctga tgctgtttgc agaatcaatt 13560
agcatagccc tttcaaagag gaattctacc agacatttga agtcatggaa atgtccatag 13620
tagttttcca atgtgtgtgt gtgtgtgcac gtgtgcatgt gtgtctgttt gttgttgttg 13680
ttttgaaaca gagtttccct ctatcgccca ggctggaggg caatggcatg atctcagctc 13740
actgcaactt ccacctcctg ggttcaagtg attctcatgc ctcctgagta gctgggacta 13800
caggcatgag ctaccatggc tggctaatag gtatattttt agtagagatg ggtttttgcc 13860
atgttggcca ggctggtctc aaattcctgg ccccatcctc aagtgatttg cccgcctggg 13920
cctcccaaag tgctgggatt gcaggcatga gccaccgtgc ccagccttca tagtagtttt 13980
atcctacaca gataattcaa ccccccatca aaaaaaagag agacaaaaac tataatcatg 14040
aagagataca tggaagtgta tattcatatc catcagtagg aaagtgacca attttagcct 14100
gctaacttac gcttgaacac taaaccacag acagccaata gaaaggataa ttagatgtca 14160
tctggtagaa attgcaactc tgtaaacttt ggcatgtatt tgtatttttt atttcttatt 14220
tttgttactt aaaaaaattt tttattcact tttatactga aaagttgcaa gtggtatgta 14280
tttattgtca agaatagaaa ggggccgatc atggtggctc acacctgtaa aagaatagaa 14340

-continued

```
aagtaggcca ggcatggtgg ctcacgcctg taatcccagc actttgggag gccaagacgg  14400
gcggatcacg cggtgaggag atcgagacca tcctggctaa cacgctgaaa ccctgtctct  14460
actaaaaata caaaaaatta gctgggtgta gtggcgggcg cctgtagtcc cagctacttg  14520
ggaggctgag gcaggagaat ggcgtgaacc cgggaggcag agcttgcagt gaaccgagat  14580
cgtgccactg cactccaggc tgggcgacag agcgagactc catctcaaaa aaaaaaaaaa  14640
aagaatagaa aagtaatgtg gaaaaatgac aggcaattga tttgttagag gagtaggttt  14700
ccaggtaact tgtttttctt tttctttttc tttttttttt tttttttgag acaaagtctc  14760
cgtcacccag gctgaaatgc agtggcacga tcttggctca ctggacctcc gcctcccagg  14820
ttcaagcaat tcttatacct cagccttctg tgtagctggg attacaagtg tgcaccaccc  14880
cacccggttc agataacttc tttttttttt ttctgagaca aggtctcact ctgcccccca  14940
ggctggagtg cagtggcatg atcatggctc aatgcagcca caatttcctg gctcaagaga  15000
tcctcctact tcagcctccc aagtagctgg gactatgggc gcacactgct gtacccagct  15060
aatttttaat tttttgaaga gatggggttt tgccatgttg cccaggctgg cctcgaactc  15120
ctgggctcaa gtgatccacc cacctcaacc tcccaaagtg ctgggattac agacatgagc  15180
catcacactg gcgtttctta tttgttttta aatgtccgtt gtaacagtat ttgcttaata  15240
gaaacaggtg ctaaactgag gtttgagagt tatctctaaa tcacattgat ctgttcctcc  15300
agtagttata aattacgaac attaagttac ctgtaattaa tggagcaatc caccagagca  15360
ggctacacaa tttgcaagac ccagtgcaaa atgaaaatgt gagacccttt atttaaaaag  15420
tattaagaat ttcaagatgg caaccgcaga gcatcaaatg aagtgccttt ctgagaacgg  15480
gcttgatgtg agcgcacagg tcacatgtca ggaagttggc cctaccctca gcattcagca  15540
aacattacac cctagagcta aacaagaagc ttgttgtgag agtcacggct gatgtattga  15600
cttaggcttg atgctgattt atgggctcct tggccttgaa caaggaagta cgtttactga  15660
ttttcagagg agatgcttct aaaaatggga taaaacgtta ttgcattaaa aaaaaaaacc  15720
tttgatagag tttcatttga taaactaacc tgtttcactt tgtcttcttt tcaaaaagca  15780
ttttatagat attttctcag ggataaaggt tggttttatt ttttatttat ttatttattt  15840
attttgagac agagtctcgc tctgtcatcc aggctggagt gcagtggcgt gatctcagct  15900
gactgcaact ttcggctcat tgcaacctgc ggctcactgc agcctccgcc tcgtgggttc  15960
aagcgattct cctgcctcag actcctgagt agctgggatt acaggcaccc accactacgc  16020
ccggctgatt tttatatttt tagtagagac agcttttcac catgttggcc aggctggtct  16080
cgaactcctg acctcaggtg atccgcccac ctagcctccc aaagtgctgg aattataggt  16140
gtaagccatc acgcccagcc tagaggttgg ttttagtaaa agaaacatag gttagggtac  16200
atgtgaatat tcctgttaga aaaaggtgaa atcggggatg atttcttttt ctttttcagt  16260
ttgtagattt gataatggaa gagggccttt gcatttgttt ttagatactt tgttttagat  16320
acaaacatgt gtttgggact ttttattagt tttgaggctt gtgagactta aatttccacc  16380
gtgtttctct acaataaagc attgctatga ttaaaaatga agatgccttt gtttttttgac  16440
agagtatcaa gaccaaaatt acatggagca cttgatggga gaatttcaag tctaaatcat  16500
gggtagcaga cagtggctgc aggctatttg gctcccagtg tttaattttt tttttcttca  16560
atttgttgcc aacattaaga aatctggact tttcacttag aaaaaaataa taataaataa  16620
caggaaaaaa aaccaatcct gatgtcagtt ttccttgaaa atgcagacag tcgggcagca  16680
```

-continued

```
aggccccttc cagatcacgc ctcctggtct actgccagcc cctctctcag acctgcccag  16740
ccctgtcttc tcaaacattt gtttttcatt ttcttctgat tttaatagca atccatgttc  16800
tttatagaaa atctggacaa tctagaaaag tagaagaaaa taaaataacc tgttgttcta  16860
cactctaaga ataatcacta ttctcatttt attttacttt ttattttatc ttatttattt  16920
atttatttga gacagagtct tactctgttg cccaggctgg actgcagtgg cgtgatctca  16980
gctcactgaa acctccgccg cctgggttca agtgattgtc ctgcctcagc cttccaagta  17040
gctgggatta caggcgcccg ccaccatgcc tggctaattt ttttgtattt ttagtagaga  17100
tgcagtttca ccatgttagc taggctggtt tcgaactcct cacctgaagt gatctgcccg  17160
cctcagcctc ccaaagtgct gggattacag gtgtgagcca ctgcacccag ccattattct  17220
cattttagac tttttttttct aaattcgttc tcttgtttga aaattgtgtg tgtgtgtgtg  17280
tgtgtgtaaa ccaaaccaga ctggggtcac acttctgggg tctatttcct tttttatttt  17340
aacttgatgt agttaaatgt gagcattttt tcatgtaatt atttctgtgt ggacattgta  17400
tgtttcatta tgtgacatat cacatgtgtt gtatttaact tttccccagt catgggcgta  17460
gacagttggc agcttgtgcc tgtcctaagt catgacctcg tacatgaatc atatctggtt  17520
attttcttac acttctagaa gagaggttgc tgggtcaaag gggatggact tacttaatgt  17580
ttttgtgagt gacctcacaa aggctggaca tagctcttga gtcccaggga caggctgagc  17640
cccggcagtg gcaggggttt gggggagcag gccctgcact gcatttgagg aagagccgtg  17700
catgttgctc ttggaggagg aggagcgggg cggttagagg gtctttaggt atctgtctac  17760
cttgaaaaag aaatcactca cctcttccag agcacgcccc tcacccccga cctgagagga  17820
gaggctcgtg gtttgcgatc cctctcccca ttagggtctg tcaccctggg gctgagtagt  17880
aggtatctat ggcgggtgtc ttcatggaag ccctggccac gcatcttgaa gtggctttca  17940
tcttgtccct tgcaacttaa gcggaagatg catcttggag agggtcggag gtacagttag  18000
aagcatgtgt ggtacgtgaa agccggtggt cgtggggata cagagcggtc tccagtctcg  18060
tctcctgtct cccatggcct tgctttctgg gccatagttg ctgttgtagg gggatactgt  18120
ccgctgcccc tactcaggct cccagcagcc acctccttgg cctttctgaa gtctgtcacc  18180
taaggcaaag aggtcagagc tggggactag agtcccacgt gggagtgtgg cattgggact  18240
ctgggaaagg cactgtcatt cacaaggatg tgtggccatg tatttggcaa ggttttcata  18300
tgggtgagac aaatcctctt tgaatgggca gctatgggtg gaaagaaact ccgcaccagc  18360
aggaagcagg actggagttt gtattaacac agttccattc ccaaaacata ggctacagag  18420
actgagtttg aagtattaaa atcagttatg ggatggaatg ggagaaaata tttgcaaatc  18480
atctatctga caagggactt gtatccagaa tagataacga actcttacaa ttcaacaatt  18540
agaagacaaa taacccaatt aaaaaccaca gctgggcaca agggatcaca cctgtaatcc  18600
cagcactttg ggaggccaag gcaggaggat tacttgagtc taggagttca agaccagcct  18660
gggcaacaag gagagacccc caactctaca aagaaattaa aaataaaaat aacagtagca  18720
gccaagcaca gtggctcacg cttgtaattt cagcactttg ggaggccgag gtgggcggat  18780
cacatgaggc caggagtttg agaccagcct gaccaacata gtaaaacccc gtttctacta  18840
aaaatataaa aattaaccag gcatgatggt gcatgcctgt aatcccagca cattgggagg  18900
ccaaggcagg tggatcactt gaggtcagga gtttgagacc agcctggcca acatggtgac  18960
accccatctc tactaaaaat acaaaaatta cctgggtgtg gtggctcaca cctgtagttc  19020
cagctactcg ggaggctgag gcacaagaat cacttgaacc caggaggtgg aggttgctgt  19080
```

```
gagccaagat tgcgctactg cactccagcc tgggtgacag agcaaaactc catctcaaaa  19140
aaaaaaaaaa aaaaagcggg ggggaactgt atggtacata taaattgtat ctcaataaac  19200
ctgcgttttg aacaaaagct ctggggaaac tattacacat gaaacagaga attctgtgaa  19260
ttgaaatcct tttttccttc ccagcaccga cagtaaatgg ttcacggccg acatcatgtc  19320
catagggtg aattgtacac agatcacagc aacagagtgt gacttcactg ccgccagtcc  19380
ctcagcaggc ttcccaatgg atttcaatgt cactctacgc cttcgagctg agctgggagc  19440
actccattct gcctgggtga caatgccttg gtttcaacac tatcggaatg gtaagagaac  19500
ttgagtatag aacttccttt atactttcca ggttttcttc acttgcggta tcgactccac  19560
acacctctgt cctgcctgtc accctaaatg accagcagac aaatgggtag gacagtcaaa  19620
cccacactct gaccttggag gctgatgcta agggagtgtg atttgctaaa ccaggggttg  19680
gccaactaca gcctgcaggc caaatcgggc ccaccacttg tttttgtaaa taaagtttta  19740
ttggaacaca cagttacatc catcttttat tgtgtctatg actgctttca cactacaatg  19800
gtagagtagt tgcaatagca gctgttgagc ctgcaaagtc taaatttact gtggctcttt  19860
actgaaaaag tttgccaacc tcatgctaga agggatgcta gcatatctct ctgatcaccc  19920
ttacttattc tggtgcaact tcttttgtgt tgcagaatag gcaccttgaa tggtgcctgg  19980
catgtagtag gtattcagta aatatttgtt gaatgactga gtgaacaaat atgtccccag  20040
atattggaag gagacagaag aaccctcaga ttccagttcc tacatttgtt cctccagtaa  20100
ttcatttgtc acgtagtcag ccatgccaga tgtttcttcc gtgtctggtt tatgcacaca  20160
cagggcatga aacttacatg gatcttgatt tagacaaact aatgtataag acaattgaaa  20220
tgtgatcacc gtctagatat ttgatatata atgaacaatt ttattgttga cttattttca  20280
gtgttataat ggtgttttgg ttatgatttt taaaggagga ggaggtctgg ttaagatgtt  20340
aaagtttatg ttatgtgtat tttaccacaa taaaaaattg ggggaataaa aagagttcct  20400
gctgggcgcg gtggctcacg cctataatcc cagcactttg ggaggccgag gcaggcagat  20460
cacttgaggt caggagttcg agaccagcct ggccaacatg gtgaaacccc atctctacta  20520
aaaacacaaa aattagctgg atgtggtggt gcatacctgt aatcccagct acttgggaag  20580
ctgaggtagg agaatcgctt gaaccgggga ggcagaggtt gtggtgagct gagattgcac  20640
cattgcactc cagcctgggc aacaagagtg aaactccatc tcaaaaaaaa aaaaaaaaaa  20700
aaaaaaagca aaataatcca aagaacagga gggacaagga caaagcttcc aggcatagaa  20760
gaaacaaaat tggccataag ttgacagttg attcagttgg gtaattagta catgagtgtt  20820
tgttaatgat cttccctcta cttttttttt tttttttttt ttgagacgga gtctctctct  20880
cttgcccagg ctggagtgca gtggcgcaat cttggctcac tgcaagctcc acctcccagg  20940
ttcacgccat tctcctgcct cagcctcccg agtagctggg actacaggcg cccgccacca  21000
cacccggcta attttttgta tttttagtag agatggggtt tcaccatgtt agccaggatg  21060
gtcttgaact cctgaccttg tgatccgccc gcctcggcct cccaaagtgc tgggattaca  21120
ggcgtgagcc accgcaccca gcctatcttc tctctacttt ctatgtgttt gaaattttct  21180
gtaataaaaa gttttttttt gttgttgttg tttttgaggt ggagtcttgc actgtcgccc  21240
aggctggcgt gcagtggtgc agtctcggct cactgcaacc tctgcctcct gggttcaagt  21300
gattctccct cccgggttca agtgagcctc ccaagtagct gggactacag gtgcacgcca  21360
ctatgcccgt ctaatttttt gtatttttag tagagacggg atttcaccat gttgtccagg  21420
```

-continued

```
ctggcctcta actcctgacc tcgtgatccg cccatctcag cctcccaaag tgctaggatt  21480
acaggcgtga gagccaccgt gcccggccaa taaaaagttt tttagagagg atcatgcctg  21540
taatcttagc ccattgggag gctgaggtgg gaggatcgct tgagctcagg agttcaagat  21600
gagcctgggg aatatagcaa gaccccatct ctattttttt ttttttttaa tcagtggttt  21660
gtgctaggta ctgtgaggga cagaaacaga gaagacaggg caatcctgcc agctcctcgt  21720
ctgctgtgga caagccattt gtccttgggt gccaaaccac cctccatttg agctataaag  21780
tgtcaaataa gtgggaatta ggagtatgca aacaagtaat gatggctggg cgcagtggct  21840
cacccctgca atcccagcac tttgggaagc tgaggcaggc agatcatctg tggtcaggag  21900
ttcaagacca gtctggccaa catggtgaaa ccccatctct actaaaaata caaaagttag  21960
ccgggtatga tggcacacga ctgtaatccc agctacttgg aaggctgagg caggagaatc  22020
tcttgaacct gggaggtgga ggttgcagtg ggccaagatg acaccattgc acatcagcct  22080
gggtgacaga gcgaggctct gtcatttaaa aaaaaaaagg aatgatactt accgccactg  22140
cccagggatc aagagaaggt aacagaagca ggatgtatcg tgacagtggg tccggtgcca  22200
gccagctgcc gcttccggcc ggagtcaagc acccatgttt ctgttagtta ctggctgggc  22260
tgctgttctc tgccctcgtg cttgaaaagc ttgacacagt ggtggtctca tgtcacatct  22320
gccactttca cctctgctgg tggcgttaga atcagtaatg gatatggagg tggtttacca  22380
agcagaggag tgagatggtg gttggagggg gcaggcttta gcatcaccct cacctgggtt  22440
catatcccaa ctctgccatt tattggctgt gttactgtgg gcaagtagtg tcacctcctg  22500
gcttccgttt cctcgtctga gaaatgggga taaccttatt tgtttttttg ttttgttttg  22560
ttttttgaga cagtctcgct ctgtcgccca ggctggagtg cagtggagcg atctcagttc  22620
actgcagcct ccgcctccag gtttaagtga ttctcgtgcc tcagcctccc cagtagctag  22680
gattactggc atgggccacc acaccccagt taattttggt tttgtttttg tgagatggag  22740
tttcactctt gtcacccggg ctggagtgca gtggcccgat ctcggctcac tgcaacctct  22800
gcctctcagg ttcaagcgat tctcctgcct cagcctcctg agtagctggg attactggca  22860
tgcaccacca tgccccacca tgcccagcta atttttgtat ttttagtaga aacggcattt  22920
ctccatgttg gccagactgg tcttgaactc ctgacctcaa gtgatctgcc cacctcagcc  22980
tcccaaagtg ctgggattac aggtatgagc caccatgccc atcccgtgat acccttattt  23040
ggcagtgaca ctgatcgtga gaggcttcgt ggaaaggcca tttacctgga gactccacac  23100
attgtcgtcc agtgttccct agagccagcc ttcctccagt gctgtgagag gaggcagatt  23160
gttctcgcct ctagatgagg tttactgggt tcatgtcaga ttccgggcca ggactctctt  23220
cagaagggca ggtctgagcc ctgtgttttc agccgtgcag tggccagctg tggctggtgt  23280
ccacactccc atgtgctaat ggagatgccc aaagaatgtg tccaaagcca gtccctgcag  23340
gtgcttctgc aacgcacttc tgcacactct gctcacttag ctgggacaag ggaagctgga  23400
gaacgtgtgt gctggtgtcc ctgggcaggc tgagtggaag agcattttgt cactagcagt  23460
caatccacaa acatcactat ggctggtggt gggccaggcc tgacctcact tctgccactg  23520
ggagttgtct ggacttagca cctccaccag aacaaatgag ggggcacaac tacaaactca  23580
gcagttcttt tgcacagaga gaagcttggc cagatcatac acctaaccct caccaacctg  23640
gagtgcccag gggagagaat ccagccctgc tgttgtgaac acacagtgac aggattgtct  23700
ccttgtgtaa aatgtgcaga cattggtctc ttagaacttc gaggacccaa actgtacttt  23760
gatctgagtt tctctggtga attatacaat gtgcatgctt acttaataaa tgcttgataa  23820
```

-continued

```
ccccctcattg atagcacatc atgagtcaca gtcctagcct gacctgtgaa ttatatgaaa  23880
agcctgaaca aatagactta catggcaaca cttctcagtt attgtgttta aatatagtat  23940
gggcatggtg ctcacgcctg taatcccagc actttgggag gccaaggcag gcggatcacc  24000
tgaggtcagg agtttgaaac cagcctggcc aacatagtga aaccctgtct ctactaaaaa  24060
tacaaaaatt agccgggtat ggtggcgtgt gcctgtaatc ccagctacat gagaggctga  24120
ggcaggagaa tcgcttgaac ctggaaggcg gaggttgcag tgagttgaga ttgcaccact  24180
gcactccagc ctgggtgata tgtgcgagat tccatctcaa aaatgaataa ataaataaat  24240
aggccaggcg cggtggctca cacctgtaat ctcagcactt tgggaggctg aggtgggcgg  24300
atcacgaggt caggagttcg agaacagcct ggccaacatg atgataccct gtttcttcta  24360
aaaatataaa aattagccag gcatggtggc acacgcctgt tgtaatccca gctacttgag  24420
aggctgatgc aagagaattg cttgagcccg ggaggtggag gttgcagtga gccgagatcg  24480
cacaactgca ctctagcctg ggcgacagag caaaactgtc tcgaaaaaat aataataaat  24540
aaagagatag ataaaaacgt gtgtgtatat atctacaccc actatatata tatatataca  24600
tatatatata gcattatata atacattgta ttatatctat aatacatatg tgtatgtgtg  24660
tggttttctc tttgtaattc tttttcagtg actgtcgggc ctccagaaaa cattgaggtg  24720
accccaggag aaggctccct catcatcagg ttctcctctc cctttgacat cgctgatacc  24780
tccacggcct ttttttgtta ttatgtccat tactgggaaa aaggaggaat ccaacaggca  24840
agagcatctt tcttttttgt ttggattttc ttttctttgc agtttctggc ttagcaaaag  24900
aaagaaacct ttaacatggg caagaacagg gtgtctccat gtccccgtgt ccccatagag  24960
gctgagccct gagcctgttt tcattgtcct cttcaagacc tgtttttcca ctcggtttgc  25020
tgagacctcc ctccgccagg ctgatctgaa gggccagcca tcctttgatg tcactctgtg  25080
tcccttgtgt ggggttgaga ctttgccggt gccctgctta cgatgccttt gccacgctct  25140
gtagtttgga ggaggtttta gtgggcctgg ttctccatga ggaatccaca actacagcct  25200
gcaaggctta actgtataaa tgtttgaaca gtttgtgaaa agggcacatg cgaaatcggg  25260
gggaaacaga gggagaaaga gctttccaga gagcagtacc agcaggtatg agaaggcgtg  25320
gcatacgtgg agaactgcag gtgcttagat tggtcagaaa tgcaatccac aaggggctgt  25380
ggcaggtgct cacgttgaca gaggtgcatg acatcagagc ggcctggtca gcctcgggga  25440
gtataggaaa aagcatcatg gtcttgaagc atctccagtg cctaaattat cctagctgca  25500
tttaaggagg ttctgttatc tatgggaact tcatgatttc ctaaattcaa cattatgatg  25560
gtttttgata ataagagctt acatttattg agagcttcct ttgtgtttgg ctctgggcca  25620
gaattttaga tacttcatct catttcatct tttttttttt tttttttttg agctggagtt  25680
tcgctcttga tgcccagcta gtttttgtat ttttagtaga gacagggttt ttaccacgtt  25740
ggtcaggctg gtctcagact cctgacctca ggtgatctgc ccaccttggc cacccaaagt  25800
gctgggatta caggcatgag ccaccgtgcc cggcccattt catctttata ctaatccgtt  25860
tgcagagaga gaatccaagt cgttaagtgg cttgcctcag gtcagcagcg aatcactggc  25920
agagcagagc agagcagaga tgcctagctt cagagccctg ctcttgacca ccatcttttt  25980
ctgccacacg ctttgtatct gcacttctcc ttcatttttt tttttttttt aattattgtt  26040
cttttttttga gacagtctca ctgtcgccca ggctagagta ctgtggtacc atcttggctc  26100
actgcaacct ctacctcccc ggctcaagca gtccacccac ttcagccacc cgagtagctg  26160
```

-continued

```
gaactacagg cctgtgccaa ccacacctgg ctaatatttt taaatttttt tttatagaga  26220
tggggttttg ccatgttgcc caggctggtc tcgaactcct ggtctcaagc gatctgccca  26280
cctcagtctc caaaagtgct gaggttacag gcatgagccc gttcccagcc tcctcttcat  26340
ttcattatgg ggaatatgaa actgggaaga gtgagactca ctgaaaaaca gacttagcat  26400
ctaggaaata gggaaaaatc atttctccat atcagagctc aagatctggg tcgattagaa  26460
tagagggagc ctggcagaat ccagaagaga gactctgcct cttccaagtc tgtcctctcc  26520
aactggatac ggtgccggaa atgcaagaga taggatgggc cctctggcca cgcttttctc  26580
caccctttgg ttgctttctt cactcgaggg caccgtgttg ccatgctccc tccccaaggg  26640
cccgcccata cttttgtttt tttaggatgg agtccatcca cttctctgca ctgagtcagc  26700
ccccagaggg cgagttgcca cttgtatcct agagctgggc agggctgccc agcactggag  26760
aactcagctc caggaccctg ggccagcct tgttgagcag caagctctaa tgaagagcac  26820
acagaacagg cttccactgc ctgggacccg cttagcacca tgtcacttag cctctctggg  26880
ctgcagcttc ctcgtgtata aaatgaaaca actgagctat aagctggagc ctgtgaagag  26940
gagcagccgt gagggccccc aagtcccttt cctccatttg accagagcat ctgtacttgg  27000
cttccatgat caaaaggttc aaggatgaaa atgactctga aagccaccaa tgtgatcttt  27060
gttccagctg tgagtctgtg tgttagggtc cccaagaccc accctagatc gctcaaagga  27120
ctcccaggac tcagcacaga gtcacactct gatttcgttt tgagacagaa tttcactctg  27180
tctcccaggg tagagtgcag tgccacaatc tcggctcacg ggttcaagag attttcctgt  27240
ctcagcctcc acatctgtgc ctggcccata ctctgatttt ttatagcaaa aggatgcaaa  27300
gcaaaatcgg caaagggaag aggcacatgg aggaaagtcc gcaggtgtcc aggggtaggc  27360
ttccaggagc ccttcctgag ctgagtcacg caggatacac ttcattgctc caccagcaag  27420
ctgtgactgc acatgtgaac tgttgtctgc cagggaggct tatgagagac ccagcgccca  27480
gggctttttc tgggggctgg ccacatacgc accctctgtg tagcgtatgc caaaattccg  27540
actcccagaa ggaaaacaga tgttcctcat aaagaaaaca cattgtgcaa acagtgtagg  27600
gacggtaagc caccttacca gtttgggaat gggagggata aacttgaaat ccaaattccc  27660
aggctgggcg cggtggctta cgcctgtaat cccagcactt tgggaggccg aggcaggcag  27720
atcacttgag gtcaggggtt cgagacaggc ctggctagca tggtgaaaac ccatctctac  27780
taaaaataca aaaattagcc aggcgtggtg gtgggcacct gtgatcccag ttactcagga  27840
ggctgaggca ggagaattgc ttgaacctgg gaggcagagg ttgcagtgag tcgagatcac  27900
actactgcac tccagcctgg gcaacggagc aagactccgt ctcaaaaaac aaacaaacaa  27960
aaaacgcaca caaattccca gatgtcagct aagggttgac ctggaaatca ggcccttcaa  28020
agggcattag tgttaggcct gttacgttag ctcttctgca gtctgtgact ctaaatttta  28080
ggaattccaa ttgaatgctg aaataaaccc aaagggaatt tttgtcctta aaatcgtgtc  28140
ttcctctgcc ctggcagtcc aacaccatta aacagaagaa aagaaaatgt aaaaccatca  28200
agtaatacta ttattcatag atcatacaat tacttttata tttttatttt ttaattttaa  28260
tttttcagag acaatttcac tctgtcaccc aggctggagt gcagtggtgc agtcatagct  28320
cactgtagcc tccaattcac aggctcaagc catcctccca ctttggcctt ccgagtagct  28380
gggacttata ggcatgcacc accatgacca gcttattttt ttattattat tttctgtaga  28440
gacggaggga gggggtctca ctatgttacc caagctcaaa ctcctggact caagtgatcc  28500
tcccacctca gcctcccaaa gtgctggaat tacaggcatg agccaccatg cctggcctat  28560
```

-continued

```
ttttgtattt taaaaaataa caacatgttc tgtatttgaa taatctgcct tttttcagtt  28620
aacaatttag cagccttgtc ttcccatgtt ttcaagcata tgttatacca ccatttcatg  28680
tggctgtagt ggattatatt gtatctcaaa attagaaaac agttctttgc aagaaaccct  28740
atactgccat aatagggtat cgctgttttc cactttggta tgggacaatg acagccttgc  28800
caggacaaca ggagccattg cctggaagac caggtgggga ggcagcaagg cctgctcaag  28860
gcagcagagg gatgcgcaga ggagacacag aaccttccta gagtctaggg tccagttgtc  28920
tcctgatgac ataaatcctt aaggtcattt tagctgaaac tataggaggc tcaagcacat  28980
ttcggtcaaa ctagaagcag gttgggaatg aaaggaacat tatttcccag aataattttt  29040
tctctgttga ctaacttgag gtatctagat taaccgtgag atacaaaatg ttggccaggc  29100
gcggtggctc acgcctataa tcccagcact ttgggaggcc gaggcaggtg gatcacctga  29160
gatcaggagc tcgagaccag cctgggcaac atggtgaaac cctgtttcta ctaaaaatac  29220
aaaaatgagc cagacatgat ggtgggtgtc tataatccca actactcagg agttggaggc  29280
aggagaattg cttgaacctg ggaggcggag gttgcagtga gccgaggtcg caccattgcg  29340
gtccagcctg gtgacagagc gaaactccat ctcaaaaaaa aaaagaaata caaaatgttt  29400
gttttgagat ggagtcttgc tcttcatcca ggctggcgca atctcagctc actgcaccct  29460
ctgcctcctg gtccaagtga ttctcctccc tcagcctccc atgtagctgg gattacaggt  29520
gtgtgccacc acatccagct aatttttgta cttttagtag agactgggtt ttgcaatgtt  29580
ggccaggctg gtctcttaac tcctgacctc aggtgatcca cccaccctgg cctcccaaag  29640
tggtgggatt ataggcgtga gccaccccat ccagcccaaa atgttaaagg agaaaaagat  29700
tatcctagaa attgggattt actgaagtct agttactaca atgggcactc tgagacctca  29760
cagccagaaa cacagttcta aagctatcag cctctttggc cacacaacac accaattttc  29820
acacataaaa tgtgtccact gccagccagt gacccactaa aaatggcatc ttgttcttct  29880
ttggttgtcg tgttcacagt gaatttgagg aaacatcaga aaagatgtag gcagcttggc  29940
catgttcatt tacatgtgtg cttgtgatgt ttttaaaaca ggtcaaaggc cctttcagaa  30000
gcaactccat ttcattggat aacttaaaac cctccagagt gtactgttta caagtccagg  30060
cacaactgct ttggaacaaa agtaacatct ttagagtcgg gcatttaagc aacatatctt  30120
gctacgaaac aatggcagat ggtaaaatat accttcttat gtcctttctg aactgggaaa  30180
agaatactcc tccaatagtg aaatcgggga atgcttatga ggtcatgggt ggtgggagtg  30240
gggagaccca gtgagaagag tgctgaactg caggaataat gagcttgtgc tgagatttgc  30300
agtagtggag gctaccagac agctaccact tgctttattt cattacagga ttgactttag  30360
ctattaatgt aagcatacca ggtgagggtg gggggtagag ggacttgccc attttactag  30420
gacaggaatg ctctttaagc agcatggatg gaacattaac tgatgtttgt gttgtgcgta  30480
ggaagatcat tctgttcact ttcgtgtcct ctttttagcc tccactgagc ttcagcaagt  30540
catcctgatc tccgtgggaa cattttcgtt gctgtcggtg ctggcaggag cctgtttctt  30600
cctggtcctg aaatatagag gcctgattaa atactggttt cacactccac caagcatccc  30660
attacagata gaagaggtac gtgtgcacac atctcttttt ttttttttga gacagggtct  30720
tgctctgttg cccaggcggg agtgtcatgg tacaatctct gctcactgca gcctccatct  30780
cccaggttca agcgattctc ctgcctcagc ctcctgagta gctggtatta caagtgctca  30840
ccaccatggc ctgctaattt ttgtattttt ggtagaaaca gggttttgct atgttggcca  30900
```

-continued

```
gactggtctc aaactcctga cctcaagtga tccacccacc tcagcctccc aaagtgctgg  30960
gattacaggc gggagccact gcgcccggcc acgcagacat cttaatggtg acacatcagg  31020
gccccactgc ccctggcaac ccctaagagt gcagctgtgg gcaaagccgt ggacacagag  31080
atttgggtta caaatggtat ggggttgttt gtacacccat gttcatgttg acacgattca  31140
caacagccaa aaggtggaag cactccggtg tcgttgaagg attaatagat aaatctttaa  31200
tagatggtct ttccatacaa tggaatatca ttcagcctta gaaaggaagg ggattgtgac  31260
acatcctacc acacacatgg accttgagga cattatgctg agtagagtag ggcagtcaca  31320
aaaggatact gtctgcttcc acttaaatga ggtccccaga gtcatcaaat ccataaagac  31380
aggaagtaga atggtggttg cggtggtgga gggagggaag tgggaagttc gtgttgaatg  31440
gggccagagt ttcagttctg ggctgtacaa gagttctgga gatggatggt ggtcatgatt  31500
gcacaatgtg aatgtgcttg gcactaccga actgtacacc taaaaagagt tatgatggta  31560
cattttatgt tatgtgtatt ttaccacaat ttaatttttt ttttttaatg gcatggggtt  31620
ggctaaaaag gtggcctggc ctggagattg gctgcagtag acccctctcc gaggcagcag  31680
gtctcctctg ctgtctggag aatgctccag ggaagtggcc tggctggagg acgtgaaggc  31740
ggtggagaca gtgatcagga gcttgagctt tggggcccac agggtgctta ggagggccct  31800
aaggcagagt caacacccag agctgtgagt gccaggcccc gtgtacccat tgcccagtgg  31860
gtattgctaa tatttgaaag gacttgagaa agaacagtag cgtgggtctt gtggaaagtc  31920
ttattttcct gcataacccc agccccctga ggctctgtga ggccattggg ccttctgagg  31980
acacggtcag gacattttgg ggatcagagg cgagctgaga gaagaacatt taaaaagcat  32040
ttgcagccgg gcgcagtgac ccacacctgt aatcccagga cttggggagg ccagggtggg  32100
cagatcacct gaggtcagga gttcgagacc agcctggcca acatggtgaa accctgtctc  32160
taccaaaaat acaaaaatta gccgggcgtg gtggtgggcg cctgtaatcc cagctacatg  32220
agaggctgag gcaggagaat tgcttgaacc caggaggtgg aagttacagt aagccaatat  32280
cgcaccatag cactttagct tgggtggcag agcaagactc catctcaaaa aaataaaata  32340
aataaaaagc atttgcttct ggaggcttca cattattctt gggtaaacct agagtaaagg  32400
tgttggaagc agaatgttac tcagttacat gtgggatgaa cagaggttag ataaggtcca  32460
agtctgcaga aacatagcag cactttcaga aagaacccta gtcacttgtt ccttcatctg  32520
ccatgatgta ttgtaggtac acaggcagta tacagattcc ctactagaac ctccctggtt  32580
aatattgtca caaaatcaca gctcctaaca ggtctcagaa tcttacttgc agtaataatc  32640
tctctctctc ctggtagaac taccagctga gccccagtac atgaatatac tatgagtcat  32700
tcctctgaga catgaacaga aaacacaggc ctgtcagttc acttttctag gaaagcataa  32760
agaacatccg ccaaaggtct ctgagttaca tgggaacagt gaatcatgtt tcacttataa  32820
ttctggggtt tcacaagggt acatgttttg gttttgttcc tctttcagtc agtcagctac  32880
aagcttattg tcttccagta tctttcagca tttccaagag ctagacacta gattcttggt  32940
aacttggtga atctatggct aagcctaaag cctgcgggag caaaagggaa attaatcgct  33000
gggaaacacc cctttatatg ttaaggccta aggccctcgc tcccagattc tctgcttgct  33060
gtgcgctggt gcaaggggag gggtggagga gtgcctgaga ccaatgcttg tgaacttgcc  33120
ctctttttcc ccatcacagc tgaacaagag cccccagtcc ctccttcact gaaaggttac  33180
aattttagag acgtcttaag attaataacc cacaggccta cactgagggt tgcaaggaag  33240
aacttgcttt tcttccaatc agaaaatcag aagaaaaaaa caaaacttgc ttttcctgag  33300
```

-continued

```
ttttgccctt ttaaactctc agcatattaa catggtcagc cctgggatga gtattaaagt  33360
gattactgag atgaggggta aggagtattc aactattaga agttgttggc tgggtgaggt  33420
ggctcatgcc tgtaatccca gcactttgag aggccgaggt gggtggatca tgaagtcagg  33480
agatcgagac catcctggcc aacagggtga aaccctgtct ctactaaaaa tacaaaaatt  33540
acccaggcat ggtggcatgc gcctgtagtc ccagctactt gggaggctga ggcaggagaa  33600
tcacttgaac ccaggaggcg gaggctgcag tgagctgaga tccacgccac tgcactccag  33660
cctggcaaca gagcaagact ccgtctcaaa aaaaaaaaaa aaaaaaaaaa aattagccag  33720
ccgtggtggt gcacgcctgc aatcctagct acttggttgg gaagctgagg caggagaatt  33780
gcttgaaccc aggaggcgga agttgcagtg agccgagatc gcgccactgc actccagcct  33840
gggcgaaaaa gagactgact caacaacaat aaaaaattgt tgccgggtgc agtggctcac  33900
acctgcaatc ccagcacttt gggaggccga ggcgggcgga tcacctgagg tcaggagttc  33960
gagacagcct gaccaacatg ggaaaccccg tctctactta aaatacaaaa ttagcagggt  34020
gtggtggtgc atgcctgtaa tcccagctac ttgggaggct gaggcagagg ttgcagtgag  34080
atgagatcgt gtcattgcac tccagcctgg gcaacaacgt gaaactccgt ctcaaaaaaa  34140
aaaaattgtt tcattgttga ataaaaagaa aaataagtta tgtcattggt ggacagaatc  34200
aacttatatc tgaataaaat aactatacca attaaaacta aagtaggcca ggcgtagtgg  34260
ctcacgccta taatcccagc actttgggag gccaaggtgg gtggatcatt tgcgatcagg  34320
agtttgagac cagcgtggcc aacatagtga aaccctgtct ctactaaaaa tacaaaatta  34380
gccaggcaag gtggtgggca cctgtagtcc cagctacttg gaggattgag gcaggagaat  34440
cgcttgaacc tgggaagcag aggttgcagt gagctgagat cacaccacta tactccagcc  34500
taggcaagag taagactcca tctcaaaaaa aaaataaaaa taaaaataaa ataaaaacaa  34560
aaactaaagt taaaaggtct ggtatactga actggtaaac taattacaat tttgctttcc  34620
aacctcctca agtatttaaa agacccaact cagcccatct tagaggcctt ggacaaggac  34680
agctcaccaa aggatgacgt ctgggactct gtgtccatta tctcgtttcc ggaaaaggag  34740
caagaagatg ttctccaaac gctttgaacc aaagcatggg cctagcccac tggctccctg  34800
gaagagatca agccatcgga gctgctagag ttctgtctgg actttccaga gaccagtatt  34860
cccttttgct gcctctaaaa ggcctgtccc tgcagacatg agagacagca ggtctcatgg  34920
gggtgacaag cttttttttt ttttcttaaa gaattttcaa aatcaaattc cagaatgatt  34980
ttacggagat atcccaggaa aattaaggct tctcttaaac actaaaaagg catgtaattg  35040
cttgttagca aaatggatat gacacatctc tgatactttt ttcattattg gttgggctga  35100
gcagtcagaa gacctggtcg tcgtcttgac tttggcaaat gagccggagc cccttgggca  35160
ggtcacacaa cctgtcccag cgagggacac cgagtggccc ttcatgtaca tccatggtgt  35220
gctggcttaa aatgtaatta atcttgtaaa tatactccta gtaatttaag attttgtttt  35280
taaactggaa ataaaagatt gtatagtgca tgttttttaa agtctatgtg aagtgttttc  35340
tttattgtag cctattttct gcagagtttc agctttctaa aattactcaa tctaaacttg  35400
ttttttctta aataacacct gctagagcta ctgaggcctc atgggaactc agcaaacact  35460
tcctatggat gtcacttgat cctccaaagg ttataaagaa ggccagggcc tagtgcagtg  35520
gcccacgcct ataatcccag cactttggga ggctgaggtg ggtggatcac ttgaggccag  35580
gagttctaga cccacctggg caacatggtg aaaccctgtc tctatgaaaa atgcaaaaat  35640
```

-continued

```
tatccaggca tgatgacatg cacctgtagt cccagctact tgagaggcta aagtgggagg  35700
atgctttagc ctgggaggcg gaggttacca tgagccgaaa tgatgccact gcactccagc  35760
gtgggaggca gagcgagacc ctatctcaaa aaaaaaaaaa aaaagagggc tgggcatggt  35820
ggctcatgcc tgtaatccca gcactttggg aggtcaagat gggaggatcg cttgaggcca  35880
ggagtttgag aacagcctgg gcaacatagt gagaccttgt tttcacaaaa aataaaaaat  35940
tagctagtcg tggtggtgca cacccgtagt cccagctact caggaggctg agaccagagg  36000
atcatttgag cctaggagtt aggagttcaa ggctgcagtg agcaatgatt acaccactac  36060
attccagcct tggcaacaga gcaagagacc ctgtctcaaa aatataaaag ttataagggg  36120
gatttgcaga aggcacatta gcacttcatt tatatgtgac aagtcacact gtgttgacca  36180
aggcagggat ttgtgggcaa taaagagaat taactgatta atcaatagta atgttatcta  36240
ctgagcacgc aagtcatctg attgtgtcag tactgtcggg ctctgttgtt caaaggatat  36300
gtatttaaaa tccatttata ggctgggcac ggtggctcac acctgtaatc ccagcacttt  36360
gggaggccga ggcaggcaga tcacctgagg tcaggagttc gagaccagcc tggccaacat  36420
ggtgaaagcc tgtctccact aaaagcacaa aaattagctg agtgtggtgg caggcaccta  36480
taatcccagc tacatgggag gcagttgggg ccctgtactg ctggtaagaa agtggctttt  36540
tttttttctt ttgagacaga gtctcactct gtcgcccagg ctggagcgca gtggcgcgat  36600
ctcagctcgc tgcaacctcc acctcccagg ttcaagcaat tctcctgcct cagcctcccg  36660
aatagctggg attacaggcg tgcaccacta tgcctggcta atttttgtat ttttagtaga  36720
gatggggttt caccatgttg gccaggctgg tctcgaactc ctgacctcat gatccaccca  36780
ccttggtctc ccaaagggtt gagatcacag gcgtgagcca ccgtgtccgg caaaagtggc  36840
taactctctt aagtgttgtg taccatgctg tctgcagtgg caagagttag aaaaacaagg  36900
cccactccca ccccatgcac acaagtctcc ctgtgaagca tctgttgtat gcattaggtg  36960
caccttaagt agacaagttt ggaggaagaa gttgtagata ggagttgtaa agacttacct  37020
tagaccgttc aggaaatcgg agacagaaga gcttcttctg ttgggcagca ggatggtggc  37080
cagcgaggag tggaggatac atctatagca ggagaacagg aaagagtttc agcccagcag  37140
gacagagggc aaatcaactc tgttagggta agtgcatctg tgccacccca tttatttatt  37200
tagagacaca gtctcaccct gttgcccagg ctggagcgca gtggcacaat ctcacttcac  37260
tgcaacctct gccttccggg ttcaagcgat ttttgtgcct cagcctccag agtagctggg  37320
attacagatg tgcgccacca cacccagcta atttttgtat ttttagtaga gatggggttt  37380
cactatgttg gtcaggctgg tctcaaactc ctgacctcag gtgatccgct cacctcagcc  37440
tcccaaagtg ctgggattac aggtgtgagc cactgtgccc agccttaaat agtattttct  37500
gaaatgaaat gcctcattct ccttagtaaa ataaatgact aattgatggg attagtattt  37560
acactgtcaa ggccaggcgc agtggctcac acctgtaatc cgagcacttt gagaccctga  37620
ggtgggtgga tcatgaggtc aggagtttga gacaagcctg gtcaacatgg cgaaaacctg  37680
tttctattaa aaatacaaaa attagctggg cgtggtggct cacacctgta atcccagcta  37740
cttgggaagc tgaggcagga gaatcacttg agcccgagaa gcggaggttg cagtgagctg  37800
acatggcacc tctgcactcc agcctgggca acagagcaag actctgtctc aagaaaaata  37860
aagtcaagct aagtacattg tcaaaatttt tgagttggaa gcactcttat aaataatccg  37920
ttgacagggc ataatccata acctacttgc caaatcagcc cattccctgt ttttgtaaaa  37980
cccgtgtgct aagaatagct tttacatctt ggaatagtta aagtcaaaag aagaatattt  38040
```

```
catcacacat gaaaattcta tgatattcaa atttcactgt tcataaatat ttattagaac  38100
ccagaaggta agctgcgtgt agtggttcac acctgtaatc ccagcacttt gggaggctga  38160
ggtgggcgga tcatttgagg ccaggagttt gagaccagcc tgaccaacat ggtgaaacac  38220
cgtctctact aaaaatacaa aaattagctg ggcatggtgg tgcatgcctg taatcccagc  38280
tactcaggag gctgagcgaa gggaattgct tgaacctggg atgcagaggt tgcagtgagc  38340
agagatcgtg ccactgcatg cctggtgaca gagcgagact ctgtctcaaa aataataata  38400
aaataggccg ggtgcggggg ctcacgcttg taatcccaga actttgggag gctgaggcag  38460
gagggatcat gaggtcagga gtttgagacc agcctgacca acatggtgaa accccgtccc  38520
tactaaaaat acaaagatta gctgggcgtg gtgatgtgtg cctgtaatcc cagctactca  38580
ggaggctgag gcaggagaat cacttgaacc tgggaggcag aggttgcagt gagccaagat  38640
tgcaccactg cactccacct gggcgacaga gcaagactct gtctcaaaaa ataataataa  38700
aataaaataa cgtctctgtc catagtgttt aaatcacata aaatggactt ctggcagggc  38760
acggcggctc acacctgtaa tcccagcatt ttgggaggct caggtgagcg gatcgcctga  38820
ggtcaggagt tcaagatcag tctggccaac aaggtgacac cctgtctcta ctaaaaatac  38880
aaaaatcagc ccagcgcagt ggcaggtgcc tgtaatcaca gctattcagg aggctgaggc  38940
aggagaatcg gttgaaccca caaggtggaa gttgcagtga gcccagatga caccactgca  39000
cctcaacctg ggcaacagag caagaatctg tctcaaaaaa aaaaaggact tcttggtaca  39060
taacatttaa agaagcctgc atagtcacta tggccactat gtctttgaag tgccacaaca  39120
gagagaggct ctctgaaagg aaatgatact gatttgggaa tagggtatta caaggggaac  39180
acgtgtgcca gagtaaacta tgtacatatt taggaaggtg aaggaaaaca aaggttctta  39240
aaggaaaaaa tgaggattag atcactgttt taagataatt atccttggct ataaggatca  39300
atagcaaggg ggatgccatt ccaaggttag acaggcagtt gttgggcaga tgtcctcata  39360
gaagtgtttg ttgtgtaagg cggtgaaggg ctttgtgcaa ggttgagatt tttgcagtct  39420
tttgtgatca tttttattta tttatttatt tagagacaga gtcttgctct gtcacccaag  39480
ctggagggca gtgatgcaat cacagctcac tgcaacgtct gcctcctgga ttcaagaaat  39540
tctcctgtct cagcctcctt agtagctggg actacaggca tccgccacca tgcctggcta  39600
attttttgta tttttagtag agatgggatt ttgccatgtt gcccaggctg gtcttgaact  39660
cctgacctca agtgatccac ctgcctcaac cttctaaaat gctgggatta caggcatgag  39720
ccaccacgcc cggccttgtg atcatttttg ttatcaagca tttttgcatg agaatccttc  39780
atggccttcc ccagctctat ttgtcagggt tttttatttg tttgcttgtt tgtttgaagc  39840
acaagtgact ccattttgat tctgacaact tccacactat gcagtcacat ctctgaggcg  39900
cccagagccc ttcaaaatat atttgctgtt tgccaaatag tctctatttg agatgagaac  39960
atccccagct gtccttctgt ttgatgagaa gtgagactcc accccagcag cttccggaga  40020
tgcagtcatg cctccccacc cttcactgcc actcccagcc tcccttgaga ctcaaggact  40080
gtcccacggg aatgaagtga aagtgacgtc tttctccttg tttccagtct gtggtgaggg  40140
aaaacagctg gctacgcttg agagggtatg gaaactggtc agagtggtta cttgggacct  40200
ggggcctcag agccacccgt tgctaaggag aggactctgg tcagggcaac ttgccaatgc  40260
tctaggaatg acacctagac attcctaaaa aatgatagcc taaaaattca tcccattgta  40320
gaaatacagg cagcactagc ttctctgggc ccctcagtta tcaaaaaaag aggagggagg  40380
```

-continued

```
cagaccctca gggttacttt acatccatat acctagctac aacataaaca tcaaatgata  40440
tgtggccagg cgcgctggct catgcctgta atcccagcac tttgggaggc agaggcaggc  40500
agatcacttg aggtcaggag ttcgacacca gcctggccaa catggagaaa ccccgtctct  40560
actaaaaata caaaaattag ccaggcatga tggtgcatgc ctgtagttcc agctactcag  40620
taggttaagg catgagaatc gcttgaacct gggaggcgga ggttgcagtg agcaagatcg  40680
tgccactgca ctccagcctg ggctaacaga gagagactct gtctcaaaaa aaaaaacaaa  40740
acaaatcaaa acaaaaagca caacatatga tattaatgat tttccttgaa attaaatagt  40800
ggtatgagta acaatgtata ataactgtaa atattaattc aactcgtttc atttctacat  40860
tcaggtgaat aaaaatatct gatctattct ctgtgggtaa taagagtatt tttgtatctg  40920
aaaagcctaa gagagggtca aaccccttaaa gagctggtaa gtccaggtag gaggaccctg  40980
aggtccttgg agatgggcag gtacaaaatt ttgcctggca taaaattcaa ttaatcaatc  41040
aaactaatgt gtttcttgac tatttacttt ctgaaatttt cctgtgaccc ttaatacaac  41100
tgtgagtacc ttcaagtgtc ctccagatcc agacacttct caagtggcca gccccatgct  41160
aactactaaa atagtggagc accagtagtc ggggctgtgg gtacattcct gtaggctgtg  41220
caccgcacaa ccccacaggt gctgttgacc taaacagaac acaaaggcac acagcaactg  41280
ctagtagtcc tgatacgtaa gccactcaag ttccaaatgc ctagtcacag aagacaaaga  41340
ctgaagaacc attccaaata ttagagacac tgcagggata tgacgactaa atgcaacgtg  41400
tgaccatggg caggatcctg ccacagaaaa atagtatttt tctttactat aaagtacatt  41460
acaggggtaa tctgaagaat ttgaataagg cacaaagtac tgtatcaatg ttaattttct  41520
gactttggca tcgtatcgca gtgatgtttg gggggaaata tacacaggat tcaagggtaa  41580
gtaaacaggc gtcacatctg cagcatgctg ccaaacattt aaaataacag accaaagcaa  41640
atgtagtaaa atgttaactt ctgggaatct gaaaggttat acaggaattc tttgtggttt  41700
ttttttgttt gtttgtttgt ttttttacag agtttcgctc tgtcgcccag gctggagtgc  41760
aatggcgggg tcttggctca ctgcaacttc cgcctcctgg gttcaagcga ttctcctgcc  41820
tcagcctccc aagtagctgg gattataggc acctgccact acgcctggct aatttttgta  41880
tttttagtag agatgggatt tcaccatgtt ggccaagctg gtcttgaact cctgacctcc  41940
ggtgatccgc ccaccttggc ctcccaaagc actgagatat aggcgtgagc accatgcctg  42000
gcctctttgt gctattttta taactctcct ggtaagtctg atgtaatttc aacataaaaa  42060
gttaatctca ggctgggcgc agtggctcac gcctgtaatc ctagcacttt gggaagttga  42120
ggtgagcaga ccgcttgagc tcaggagctc cagaccaatc tgggcaacat ggtgaaaccg  42180
tgtctctaca aaaaatacaa ttagccaggc atggtggcgt gcgtctgtag tccaagctac  42240
tcaggagact gaggagagag gatctcttga gcctaggagg cagaggttgc agtgagccga  42300
gctcacacca ctgcactcca gcctgggtga cagagccaga ccctgtctca aaaaaaaaaa  42360
aggttaattt ctaaactcac aacttccatg gtgggaggga agtacactga tcacactgaa  42420
taatgttttt ggcaccagga gtagaaactg ttggagcaca gacctgtact atagtcccag  42480
ctactcggga ggctgaggct ggagggtcac ttgagctcaa gagttccagg tcgaagtgtg  42540
caatgttcat gcctgtgaaa gccactgtac tccagcctgg gtaaaatagt gagactccat  42600
ctctttacaa aaaaaaaaaa aaaaagaaag aaaaagaaac aaaagaaact gctggctggg  42660
tgcagtggtt catacctgta atcccagcac tttaggaggc tgaggtaggc agatcctttg  42720
agcccaggag ttcgagacca gcctgggtaa catggtgaaa ccccatctct acaaaacatt  42780
```

-continued

```
aacaattagc caggatgtag tggcatgcac ctgagctact tggaaggctg aggtgggagg  42840
atcgcttgag cctgggaggt ggagggtgac agagtgagac ccagtctcaa aaaaaaaaaa  42900
aaaaaaccag aaactgctgc tggaaaagag cacaatttac atcctttttg gagagctctc  42960
tggttttatg tctagacctc tggggtgggg aagaggtcaa catgctcccc aaatcaaaga  43020
cccagcactc tctacactgg cataatccat gagggtctag gcagcctgtc ctgccatact  43080
tactcaaaga aatttaaaat atcctatctg ccacagctga aagaattgaa gaggcattta  43140
ctgctatcca aaaccctaag taaaattact taagctgtga taaaagtgct acaaaaaaat  43200
gctctggcag gctctaaact tggaagtctt gtttttctta gcatggcatg ccaccttgtg  43260
gcaaaaagct aaaaagtcat cagatgagaa aggaaacatc ccttcaaaag tcatcataag  43320
aaatgccggg cacggcgcct gtaattccct gcactttggg aggccaaggc tggcggatcg  43380
cttgaggtta gaagttcgag accagcctgg ccaacatggc aaaaccccat ctctactaaa  43440
aatacaaaaa caattagcca ggcgtggtgg catgtgccta caatcccagt tacttgggag  43500
gccaaggcac gagaatggct tgaacccagg aggctgaggc tgcagtgagc cactgcactc  43560
cagcctggat gacagagtga gactctgtct caaaaaaaaa aggaaaaaaa aagcctactt  43620
gtgtgaatca cttattattt ccaggaactt tgttaagcat ttcctcagat taattctcaa  43680
acatacttac agacagggaa acagtcttgc agtcaaatag ctaataaatg gcagtgccag  43740
aataagggaa taagggagaa gtaaaccaac ctaaacttaa atccataggc ctccgagaat  43800
cccagcgccc aaaccacaac tgtctagtaa caacgcaatt ggaagaattc ttcctactgt  43860
gccctcctgc caccattttt attccccata atcaggctgg ccacaggctt ttcccaaagc  43920
cagccatgcc cacacctaaa cattttcctc tccttttgtt aattccctgt gttctatcta  43980
ttctaaagcc accatagcag cactttcccc aaattacatt tttcttttat tttttttatt  44040
ttttattttt tatttttttt tgagacagtc ttgctctgtt gcccacactg gagtacagtg  44100
gcttgatctg agctcactgc agcctctgcc tcctgggctc aagcaattct cctgcctcag  44160
catcccaagt agctgggatt acaggcatgt accaccatac ttggctaatt ttttgtattt  44220
ttagtagaga tgggtttcac tatgttggcc aggctgatct cgaactcctg acctcaagta  44280
atctgcccgc ctcggactcc caaagtactg ggagtacagg cgagagccgc tgtgcctggc  44340
cccaaattac atttttcaac atgttccagg agataaattt ccaagtctca gtaatagaaa  44400
acaccatata attgacaccc tcctcctaaa gacatacaat acacacacac acacacacac  44460
aaaaaaaaaa aaaaaaaaaa aaacctctaa gaaagaaaag aactttacag aattttaaaa  44520
aggtgttttg gagcctagtg tggtgatttg cacctctagt cccagctact caggaggctg  44580
aggcaggagg atcacttgag ctcaggaatt caagaccagc ctgggcaaca tagcaagacc  44640
cctctctaaa aaagactaag caagaaggcg gggcgcagtg ctcacgcctg taatcccaac  44700
actttgggag gccgaggcgg gtggatcacc tggggtcagg aatttgagac cagcttggcc  44760
aatatggtga aaccatgtct ctactaaaaa tacaaaaatt agccgggtag gatggtaccc  44820
acctgtaacc ccagctactc gggaggctga ggcacgagaa ccatttgaac ctgggagaca  44880
gaggttgcag tgagctgaga ttgcaccact acactccagc ctgggtgaca agagcaaaac  44940
tccatctgaa aaaaaaaaaa aaaatcaaga aataaagaaa gaaaaaacat gtttagacct  45000
agttcagccc agggtttccc aagcttcttt gacacacaca ccttttctca ggtacacctt  45060
cagggccacc agtgttctaa aagcaacttg ggaaaggtgc aactaaatct aaaaaggaga  45120
```

-continued

```
gctgagtgtg gtggtgcaca cctatagtag actgagggga ggactgcttg agccaaggag  45180
ttcaaggcag tagtgagcta taatcacacc acggcgttcc agcctgggca agagtaagac  45240
actgtaaaaa ggactccata aaaaagaaca atgaaaacaa agactcctga gttgatgttg  45300
tgactgaaaa cccttccact ggggaaaaat gtagagatca tgagttcaat gcacccatgt  45360
caaaccctct gggggctctt gctcaagggg ccaaattata tggtttgata tcatcaatct  45420
ttcagtcttc caatttcatt atgttgatgc aaatcaatgt caagtcaacg tcttgtgtat  45480
agaaatacac acacacacac acacacacac acacacacac acacatatat atatatactg  45540
gaaaaataca gcctctgggt ttttactcag tggcaacagc acaaggaata caaggatctt  45600
agagcaataa aatggaatac tctgataata ttggtccaca cacaaaaaac actcagattc  45660
aatgaccact gaatctatgt gacagcttga gaaccttagt aagggaatca catgcatttg  45720
tagatgatta ccaaagattc tgccctaact cataatattt ctaagagtgg atactaacat  45780
tatctctttt atgtttttat ttattttttta ttttctagac ggagtctcgc tttgtcaccc  45840
aagctggagt gcagttgcac gatcttggct cactgcaacc tctgcctccc gggttcaagc  45900
aattctccct gcctcagcct cccgagtagc tgggattaca ggggtgcacc accacgcctg  45960
gctaatttgt tgtattttta gtacagaccg ggtttcagta tgttggccag gctggtctcg  46020
aactcctgac ctcatgatct gcccgcctcg gcctcccaaa gtgctgggat tacaggcgtg  46080
agcccccacg cctgaccaca ttatctcttt ttttaaaatg aagaaacaga aaattaagtg  46140
atttgctcac aactaaaaaa caaattcagg gttgggtgtg gtggctcatg cctgtcaacc  46200
tagcactttg tgaggttgag gcaggtggat gtgttgagac cagttcaccc agaacagcat  46260
agtgagaccc ccgtctctac aaaaaacaac tttttttttt aatgacatgg agtcttgctc  46320
tgttgcccag actggagtgc agtggcacga ttttggctca ctgcaagctc tgcctccaag  46380
gttcacgcca ttctcttgcc tcagcctccc aagtagctgg gactacaggt gacccccacc  46440
acgcccggct aatttttttg tatttttagt acagacaggg tttcaccatg ttagccagga  46500
tggtctcgat ctcctgacct cgtgatccgc ccacctaggc ctcccaaaac attttttttt  46560
aattaaccag acataatgac acgtacctgt ggtcccagct gcttggaaag cggaggtaag  46620
aggattgcct gagctccagc atttgaaggt gcagtgagct gtggttgcac cactgcactc  46680
cagcctaggc aacagagtga gatattgtct ttaaaaaaaa aaaaaaaaat tcatggcaga  46740
gtcagaaata gaaaaaaaca gccaccattt ccagtcagtc ttcagggaaa ccttcaataa  46800
ccctcacata agcattttac aagtctattt cttcttattt tataaacata actgcatctt  46860
taattgggta tacttgaata attgaaaact gaacagcaaa tcaattttta tggttcattt  46920
tctccaacaa acaacaatat taaactgtat gagaagtaat atttattgca acaggttatg  46980
aggtggaaac aaataattag tcttacaatt tgctagaagc atgacagagc ttactaacat  47040
tttgaagaaa aaacagcaaa gaaagaagtc atcaaacaag atggtatctt gacaaaggca  47100
cagcgctcca caactgcttc atactctgtg cacaagaaat cctctcaaga gagaggagag  47160
gagtgatgcc aaatgggctt acattagagc cgtggacact accactggta ttattcatac  47220
aaccaaggct ctacaacacc cctctggaga aaaagtgcaa cacaaaatct gtgtaacaaa  47280
ggaaagcaaa agtagcaata agggcccaga ggaatacaaa cagtgcaaat acagtactgc  47340
aaactcagta aaaggagttt ttgattggag tatgaacttt caagttgaag atatatttca  47400
caggaatatt cacccaaagc ttgagagcta gagcgaggag agacttgcag tcggtaactg  47460
agtagatgaa atgcataatt tttcactagg tgataattcc ctttgggaag aagtgcttta  47520
```

-continued

```
tctttaatta ttccactttt tgttaaatgg ttcatgcttt taaactgcga ttgtctcaaa  47580
cttgcttgct attgaattgt gtaacatcag ataatggcaa gttgtcaaaa gataacccca  47640
gtggatattt gaagctgctt ttacgagaag catggtgctg agctgcctta cacagtcttt  47700
ttacagtaac cataaaaaac tgagtttatt tgatcatgta ttatcccttc tcacataaag  47760
tcatattaga ggaattcttt ttaaaagaag ctttcaaact agtcctttgg gcatttaaaa  47820
aatcattata taaaagtaca cttcttcaat acataagaac aaatattttt tctttaccaa  47880
aaaaacctca tttttaggcc aaaataagtt acaacttgct gaaaaccttt tatggctcag  47940
tgctcattct agatatatga agctatattt ttttgtacat cttcagaaat cagatactga  48000
gagtggtcct tctttttttt gagagggagt ttcactttct cccccaggct agagtgcagt  48060
ggcgcaaact cagctcacta caacctctgc cccccgggtt caagcgattc tcctgcctca  48120
gcctcctagg tagttgggat tacaggcacc caccaccatg cctggctaat ttttgtattt  48180
ttagtagatg gggtttcgcc atgttggcca ggctggtctc aaacacttga cctcaagcaa  48240
tcggcccgcc tcggcctccc aaagtgctgg gattacaggc atgagccacc gtgcccagcc  48300
agagagacaa gagtggttac ttctaaaatg acaagatgat gtaaccctgg ctcagggagt  48360
agatcaagtt ctaaatctca ggaataaaaa actgatactc attatccaat tcatatagtc  48420
ttgtattata tacatattaa cagtctatgc aatgaaaaat aaagaaattt cataaaacta  48480
tttcaaaact cagaacataa aaatgtaaag aaacaaaaca tttaatgtac aatctactcc  48540
atttggcaat gtgtactgag agataaaaaa cctatctaca aacagaatat aacaaaagga  48600
aaatgtgact taagaagtga tctcaggtcc atagctcttc ggttcttcca aatttgtaga  48660
tcagagtgct agaaagatag gaaaacaaat catgaggaaa aaaccgatgg aacaagcaac  48720
acagaattca ttttctcaat atgctttgac aggtacttca ctgattccta tcaattttaa  48780
aaattaaatt agacatcatg gcagtgttgg tcttaatttg cttattttgt aaagcagtct  48840
gttaactacg atggctaagc ataactgtat tctttcttaa ggcctgggaa gttattaaca  48900
ggcaacttgt aaggaaaaga gacatttctc tatgactcag aaacaaaaaa atgaatcaat  48960
aaatcaaaag aaaaagggag agagaccatt ctcatagtga caggcattag ggccatttta  49020
tgtctccagg agcctaccat atctaaatta cagtaactga agcaccctac aacagaccat  49080
gctgcaattc ttcattcctt caacaaataa ttattgtgca ctgaaaagtg gctacgtacc  49140
aagcacctaa gtgctggggt gagactgagt ccagacaaac ttgctcccta atggagctaa  49200
gggtctaata aggagacaat caaataaata taaaattcca cctataaaaa aatgctataa  49260
atgagaggtg cacagtatcc tcagagtgaa acataaggat cagacctagt tagagaggtc  49320
aggaaaggtt ttcctgagga gtggtgactg aattgagatc caaaagaaga gggggaatta  49380
tctcggcaaa gtgagagagg ataaggaggc gggagcagag agatgggaca ctccagggcc  49440
atgagttgag ctgtgggcat actaaatgtt ttggatttga aatgtcagca acccaagaag  49500
ggatgtgaag taggaatctg gatatacggt ttaggcctgg aaagggacat ctgtgactca  49560
ctggcatata agcaataatt ggagtcctaa gtacacatga gttcacccag ggacagaaaa  49620
ataacaagga gtttcttaag gccaagaaca gctttaagag acttcaaaag gtagtaggca  49680
gggagtggag gatcagcttg caaggaaaac agaggagtga ccagagatgt aaataaaaga  49740
ggttgtaccc cagagcttag aacaggtcca gcacacagga agcatacagg ctgcctgata  49800
acttgccagc ctctgggcag agcacataga tgacacagct gtcaactatg tccacctgag  49860
```

-continued

```
catacaaggt ttctgttcat ccaattgtca tttaagtgga ttcatctacc accacaaagt  49920
gttgaatctg aacttaatct ctaaagactg cctaaaatgt cttcataaca acttaccata  49980
tccccagaag gctgtcagtc acatgtcttt gacatataag acagcagaaa ctgccaaaca  50040
tctttcaaaa ccaggagtgt caaggccaca aggcgaaatc caggtagagc atggtggtct  50100
gagagtggag ggagaccaca tggctagagt ttgccatgca gcgtacagac agccacacag  50160
agggaacgca ggagatctgc agggggtgct ccttcagtct gtggctgagt actgaagagt  50220
ctatacataa gaggaaacta cccaagggaa ggaaagaacc actggaaaga acatgtccca  50280
gagctaccac aaggctggaa gagagttcat actctcacaa gtcgagtaga gaaacctcgg  50340
aatacatgaa gcatcagaga gtggaaacac tcaaagggta tgactgcctt agtagggga  50400
caaatcagtc ctgggctaca gctgctctgg tcctgcctat aacaaagctt aagagacata  50460
aaaggatcaa attgtttctg attgtttctg agtcacctaa ctgcatccca aaacaaagct  50520
taaaaacatt taaaggacta gcaaagatcc agtcccaaca aattgtatgc aaagcaccaa  50580
ataagggaaa ataggtccaa aatgaagagt aaacagaagc agaaaaaatc agtagaagca  50640
gatgcagaaa tgacacagac aattggacaa ggaccctgag atagctataa atatactctg  50700
tgtgttcaag gtggaagagg gcatgagcat gttaagggaa gacatcagaa atatttttaa  50760
agacccaatc aagcttctag agagagaaaa tacaatgtct gagatgaaaa aatcattgga  50820
tggcatagat tagacattgc agaagtagag attaatttat ttaattcttc aaagtgacaa  50880
tagagagatt aattttattt atttatgtat ttatttattt tgagatgaag tctcgctctg  50940
ttgctcagca atggtgtgat ctcagctcac tgcaacctca gcctcccggg ttcaagtgat  51000
tctctggcct cagccttccg agtagctggg attccaggca tgcaccacca tgcccagcta  51060
atgtctgtat ttttagtaga gatgaggttt caccatgttg gccaggctgg tctcgaactc  51120
ctgacctcaa gtgatccacc cgccttggcc tcccaaagtg ttgagattac aggtgtgagc  51180
caccatgccc agccgagatt aattttaaaa tgtaacaata gaaactatcc aaactgaaac  51240
acaaacagga aaaaaaaatc tgaccattag caagctgtga gacaacttcg agcagcctat  51300
tataacctgt aattgaaatc ccagagggag ggtgcagtgg atacaaaaaa tgcttgaaga  51360
aataatggct gagaagaatc tagatttatt gatgaactat aaacctatag atccaagaaa  51420
ctcaatatac accaagcaga aggaatatca agaaaactag accacagtac atcgtaatca  51480
aattacttaa aaccagtgac aaaagcaaag tttttcaagg cttagaagtt acttaatgat  51540
ttatgggga tggggacaga ggcagataaa attttataaa tatataccta aatatcctat  51600
gttgacatta aaagacattc attctaggct gggcatggtg gctcacacct gtaatcctac  51660
cactttggga ggctgaggtg ggcagatcac ttgaggtcag gagttcgaga ccggcctggt  51720
caacatggca aaaccccatc tctactaaaa atacaaaaat tagctgggtg tggcagtgca  51780
tgcctgtaat cccagctact tgggaggctg aggcacggaa ttgcttgagc ctgggaggca  51840
gaggttgcat tgagctgaga ttgcaccact gcacatcagc ctgggcaaca gagcgagaat  51900
ccagctcaaa aaaaaaaaaa aaaaagacat tcattctaaa aagcatagaa tggacttcat  51960
tttggggata ttttagaaga ctgcccctaa aaaatacttt taatattggt ttatttttcc  52020
acttacttta acttttctta aaagggcatt cagaaaacag aatttcccaa caggttttgt  52080
atataatatg catactatgt attaattatt attattattt tgatatggag tcttgctctg  52140
tcacccaagc tgaaatgcag tggcactatc tcgactcact ccaacccccg tgtctcctgg  52200
gttcaagtgg ttctcctgcc tcagccttcc gagtagctgg gattacaggc acacaccacc  52260
```

atgcccgact aatgtttgta tttttattag agatggggtt tcaccatgtt ggccaggctg 52320
gtctcgaacc cctgacctca gatgatccac ccacttcagc ctcccaaagt gctgggatta 52380
cagacatgag ccaccacacc tggctggcca ctaggtatta attctggttt ttcctttttt 52440
cttcataaag gtactttacc tgttgttgtt aatttttttt ttcccgaaag gctagtcaag 52500
tgaaacaatg ggtctgatag ggttttttaa taagacacag gctatggaag cagcagtctg 52560
gattcaaatc caggcttctc atttactagc taggcatcct aaagcaagcc ctaaacttta 52620
tttcctcatc tataaaatgg gaataacact gggtgtggtg gctataatcc cagcactttg 52680
ggaggccgag gcaggcaaat tgtctgagct caggagttcg agaccactct gggcaatatg 52740
gtgaaacctc gtctctacta aaatacaaaa aattagctgg gtgtggtggt gtgcacctgt 52800
agtcccacct actcgggagg ctgaggcatg ggaatcgcct gagtcccgag gcggaggctg 52860
cagtgagccg agattgttcc actgcactaa ggcagcttgg gctacagggt gagactccct 52920
cgcaaaaaat aaataaataa ataaaaataa aaataaataa aatgggaata acacctgaca 52980
tatatttaaa ataattaaat gcattatttt attttatttt ggtctcactc tattgcccag 53040
gctggagtac agtggtgcag ccttgcctca ctgcagcctc aacctcctcg gctcaagcaa 53100
tcctcccacc tcagcctctt gagtagctgg cactgtacac caccacaacc agataatttt 53160
tatatttttt tatagagaca gggttttgcc atgttgccca ggctggtctt aaactcctag 53220
acttaagcaa tccacccact tcagcctccc aaagtgctgg gattacaggc atgagccaca 53280
gcacttggcc taaatgtgaa ttcaaagggt aaaatatata aaggatccag ctaaagtctt 53340
gatacacagc aagacctcta gttaaaaggc ctctctgctc ttatgtaaca gtggaattct 53400
caccttttaa aagaagttct atcattgtaa ccaatccatg ggatttatat gtgttccata 53460
tatatgctgc cttaattaag ttgacatttc tgtaaatgtt acaggcgtgg ttaaaaaata 53520
aggcaactta cctaaaaaat ataagtgcat tttgaaaaaa cacagctagt cccggataaa 53580
catcagtatc tacatacaca aagtaaaaca gattagacgg ttatataggc aaacggcagt 53640
aataaagtat cagtgccatt cataatgata cattttgtat attacaacat actgctatta 53700
ttcattaact gtaagacatc tataatgaaa ctgaaagaag aaaatgccaa tttaattccc 53760
ccaaagcaaa ggactgctct tactctggat aaaagtcaat gaacttacaa agttttcttt 53820
tagtcaaagt aattgctggt tctagctaca tcaaaactgc tgaggaagca gtaacttgct 53880
cctttgcctc ctatggccaa cactgaaatg caaaatcgta aaaacataca aaataaattc 53940
ttgactttta aacagtctgt taatttattt tctttcatga attcaagagg ttttttgtgt 54000

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
catattaagc tttcaactct 20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide -continued

<400> SEQUENCE: 13
agtcgaaatg tttgctttaa 20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
attcgaggat tcgccccttt 20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
ttgatcgcac aattcgagga 20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
cgatccttcc ggaagggccc 20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ggcctcccag agcgcggagc 20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tcttcgggtg ctgaggagcg 20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
aggacctgct ctgcgttgta 20

<210> SEQ ID NO 20
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 20
ccactggctc ccaactcagg 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
gtagacaaca ggcctcgtgc 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
actgtcggtg tatttaaact 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
tgtcggccgt gaaccattta 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
aattcacccc tatggacatg 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
tgttgctgtg atctgtgtac 20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26

-continued

```
acactctgtt gctgtgatct                                                 20


<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27

gaagtcacac tctgttgctg                                                 20


<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28

aaatccattg ggaagcctgc                                                 20


<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29

gaaggcgtag agtgacattg                                                 20


<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30

gctcccagct cagctcgaag                                                 20


<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31

gaatggagtg ctcccagctc                                                 20


<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32

tgtcacccag gcagaatgga                                                 20


<210> SEQ ID NO 33
<211> LENGTH: 20
<212> TYPE: DNA
<213> ORGANISM: Artificial Sequence
```

-continued

<220> FEATURE:
<223> OTHER INFORMATION: Antisense Oligonucleotide

<400> SEQUENCE: 33
tagtgttgaa accaaggcat 20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ccgacagtca cattccgata 20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cacctcaatg ttttctggag 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
aaggccgtgg aggtatcagc 20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
cctccttttt cccagtaatg 20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gggcctttga cctgttggat 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
agttatccaa tgaaatggag 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gtacactctg gagggtttta 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ctggacttgt aaacagtaca 20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
cttttgttcc aaagcagttg 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
actctaaaga tgttactttt 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
cgactctaaa gatgttactt 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
taaatgcccg actctaaaga 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ttgcttaaat gcccgactct 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
ttgtttcgta gcaagatatg 20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ctcagtggag gcatctgcca 20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ttgctgaagc tcagtggagg 20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gaaaatgttc ccacggagat 20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
cgacagcaac gaaaatgttc 20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
caggctcctg ccagcaccga 20

<210> SEQ ID NO 53

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
taatgggatg cttggtggag 20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
taaatactct tctatctgta 20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
tctaagatgg gctgagttgg 20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
cgtcatcctt tggtgagctg 20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
aatggacaca gagtcccaga 20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
cgagataatg gacacagagt 20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
catgctttgg ttcaaagcgt 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
agtgggctag gcccatgctt 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ctcttccagg gagccagtgg 20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gcttgatctc ttccagggag 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
actctagcag ctccgatggc 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ggcagcaaaa gggaatactg 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ctctcatgtc tgcagggaca 20

<210> SEQ ID NO 66
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 66
tgtcaccccc atgagacctg 20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ttttgaaaat tctttaagaa 20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
caagcaatta catgcctttt 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
agtatcagag atgtgtcata 20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ttctgactgc tcagcccaac 20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
tcaagacgac gaccaggtct 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ccaaagtcaa gacgacgacc 20

-continued

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
gccactcagt gtccctcgct 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tgtacatgaa gggccactca 20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
catggatgta catgaagggc 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ttttaagcca gcacaccatg 20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
gattaattac attttaagcc 20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
atatttacaa gattaattac 20

<210> SEQ ID NO 79
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 79
tcactgggcc ctttctaact 20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
cctccttcac tgggcccttt 20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tagaaatgct ggaagtttct 20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gccggctcca gggcaaaccc 20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ttgggtgaca gagagagact 20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
aagttattct aattggatgg 20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
ttcttagagt gtagaacaac 20

-continued

```
<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86

gaggaacaaa tgtaggaact                                                    20


<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87

cctgggcgac agtgcaagac                                                    20


<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88

gctctgtcac ccaggctgat                                                    20


<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89

tctcttgcat cagcctctca                                                    20
```

ANTISENSE MODULATION OF INTERFERON GAMMA RECEPTOR 2 EXPRESSION

FIELD OF THE INVENTION

The present invention provides compositions and methods for modulating the expression of Interferon gamma receptor 2. In particular, this invention relates to compounds, particularly oligonucleotides, specifically hybridizable with nucleic acids encoding Interferon gamma receptor 2. Such compounds have been shown to modulate the expression of Interferon gamma receptor 2.

BACKGROUND OF THE INVENTION

Cytokines are small to medium sized proteins and glycoproteins that mediate highly potent biological effects on many cell types in networks or cascades. They have critical roles in hematopoiesis, inflammatory responses and the development and maintenance of immune responses. Typical properties in networks of cytokines are pleiotropy, redundancy, synergistic activity and antagonistic effects upon each other (Townsend and McKenzie, *J. Cell Sci*., 2000, 113, 3549–3550). Knowledge of how cytokine networks are comprised and operate is important in understanding how they mediate their diverse effects on biological systems (Townsend and McKenzie, *J. Cell Sci*., 2000, 113, 3549–3550).

Interferon-gamma (IFN-gamma) is a cytokine secreted by activated T lymphocytes and natural killer (NK) cells. It is involved in the modulation of a wide variety of immunological and inflammatory responses including activation of macrophages, cytotoxic T cells and Natural Killer (NK) cells, regulation of antibody production by B lymphocytes and control of apoptosis (Billiau, *Adv. Immunol*., 1996, 62, 61–130).

Interferon gamma receptor complexes are expressed on almost all nucleated cells and show species specificity in their ability to bind IFN-gamma (Dorman and Holland, *Cytokine Growth Factor Rev*., 2000, 11, 321–333). The functional interferon gamma receptor is composed of two 90 kDa polypeptides designated interferon gamma receptor 1 (also known as IFNGR1, IFN-gamma receptor-alpha chain and CD119w) and interferon gamma receptor 2 (also known as IFNGR2, IFN-gamma receptor-beta, IFN-gamma transducer 1, AF-1 and GAF).

The extracellular portion of interferon gamma receptor 1 contains the IFN-gamma ligand-binding domain and the intracellular portion contains the domains necessary for signal transduction and receptor recycling (Dorman and Holland, *Cytokine Growth Factor Rev*., 2000, 11, 321–333). In the absence of stimulation, interferon gamma receptors 1 and 2 are not strongly associated with each other. Upon binding of IFN-gamma as a homodimer to the two interferon gamma receptor 1 proteins, interferon gamma receptors 1 and 2 and their constitutively-associated Janus kinases (JAK1 and JAK2, respectively) are brought into proximity so that the signaling cascade can begin via phosphorylation of tyrosine-440 on interferon gamma receptor 1 (Dorman and Holland, *Cytokine Growth Factor Rev*., 2000, 11, 321–333). Signals are transmitted to the nucleus via the Jak-STAT mechanism of signal transduction involving a cascade of tyrosine phopshorylations of STAT proteins (signal transducer and activator of transcription) in the cytoplasm.

Human interferon gamma receptor 2 has been localized to chromosome arm 21q, a region which is known to confer resistance to the encephalomyocarditis virus (Cook et al., *J Biol Chem*, 1994, 269, 7013–7018).

Complete absence of human IFN-gamma responsiveness due to a mutation in either interferon gamma receptor 1 or interferon gamma receptor 2 is typically associated with severe mycobacterial infections in lungs, viscera, lymph nodes, blood and bone marrow (Dorman and Holland, *Cytokine Growth Factor Rev*., 2000, 11, 321–333). A clinical phenotype associated with autosomal dominant mutations of interferon gamma receptor 1 (leading to partial interferon gamma 1 deficiency is milder than seen in individuals with complete absence of IFN-gamma responsiveness and infections are usually responsive to appropriate antimicrobial therapy (Dorman and Holland, *Cytokine Growth Factor Rev*., 2000, 11, 321–333).

The expression of the human interferon gamma receptor complex is modulated by environmental signals in human malignant T cells and thymocytes (Novelli et al., *J. Immunol*., 1994, 152, 496–504). The upregulation of IFN-gamma expression promotes T cell proliferation in T cells with low levels of interferon gamma receptor complex and apoptosis in T cells with high levels of interferon gamma receptor complex (Novelli et al., *J. Immunol*., 1994, 152, 496–504).

Although IFN-gamma signaling typically exerts antiviral effects, in some cases of bacterial infections, endogenous IFN-gamma can act as a detriment to the host. In the case of HIV infection, activation of monocytoid cells by IFN-gamma signaling was found to stimulate rather than inhibit virus replication (Biswas et al., *J. Exp. Med*., 1992, 176, 739–750).

In addition, there are conflicting reports on the effects of IFN-gamma signaling on tumor growth in mice. For example, investigators have inserted the IFN-gamma gene into non-immunogenic murine tumor cells with high metastasizing potential and found that the IFN-gamma secreting cells had less ability to develop tumors than the parental cells (Gansbacher et al., *Cancer Res*., 1990, 50, 7820–7825). On the other hand, a metastasizing murine mammary carcinoma productively transfected with the IFN-gamma gene was found to metastasize more extensively than the untransfected tumor line (Ferrantini et al., *J. Immunol*., 1994, 153, 4604–4615).

In experimental animal models of autoimmune disease including: autoimmune thyroiditis, experimental autoimmune peripheral neuritis and autoimmune insulin-dependent diabetes, experimental autoimmune encephalomyelitis, autoimmune arthritis and autoimmune insulinitis, IFN-gamma was either found to facilitate induction of disease or to aggravate disease manifestations (Billiau, *Adv. Immunol*., 1996, 62, 61–130). Increased levels of IFN-gamma mRNA have been observed in intestinal propria lamina of Crohn's disease patients (Fais et al., *J. Interferon Res*., 1994, 14, 235–238).

Deregulation of IFN-gamma signaling has been implicated in autoimmune disease, complications due to viral infections and cancer. Furthermore, deregulated apoptosis signaling may impinge on other age-related disorders such as osteoporosis and atherosclerosis. Modulation of expression of components of the interferon gamma receptor complex, including interferon gamma receptor 2 may prove to be a useful strategy with which to down-regulate IFN-gamma signaling in cases where excessive signaling precipitates disease.

Attempts to modulate the process of IFN-gamma signaling have thus far been essentially limited to inhibition of IFN-gamma itself. Strategies aimed at inhibition of interferon gamma receptor 2 function are as yet untested as investigative or therapeutic protocols. Consequently there remains a long felt need for agents capable of effectively inhibiting interferon gamma receptor 2 function.

Antisense technology is emerging as an effective means for reducing the expression of specific gene products and may therefore prove to be uniquely useful in a number of therapeutic, diagnostic, and research applications for the modulation of interferon gamma receptor 2 expression.

The present invention provides compositions and methods for modulating interferon gamma receptor 2 expression.

SUMMARY OF THE INVENTION

The present invention is directed to compounds, particularly antisense oligonucleotides, which are targeted to a nucleic acid encoding Interferon gamma receptor 2, and which modulate the expression of Interferon gamma receptor 2. Pharmaceutical and other compositions comprising the compounds of the invention are also provided. Further provided are methods of modulating the expression of Interferon gamma receptor 2 in cells or tissues comprising contacting said cells or tissues with one or more of the antisense compounds or compositions of the invention. Further provided are methods of treating an animal, particularly a human, suspected of having or being prone to a disease or condition associated with expression of Interferon gamma receptor 2 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding Interferon gamma receptor 2, ultimately modulating the amount of Interferon gamma receptor 2 produced. This is accomplished by providing antisense compounds which specifically hybridize with one or more nucleic acids encoding Interferon gamma receptor 2. As used herein, the terms "target nucleic acid" and "nucleic acid encoding Interferon gamma receptor 2" encompass DNA encoding Interferon gamma receptor 2, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Interferon gamma receptor 2. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Interferon gamma receptor 2. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Interferon gamma receptor 2, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett*., 2000, 480, 17–24; Celis, et al., *FEBS Lett*., 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol*., 1999, 303, 258–72), TOGA (total gene expression analysis) (Sutcliffe, et al., *Proc. Natl. Acad. Sci. U.S.A*., 2000, 97, 1976–81), protein arrays and proteomics (Celis, et al., *FEBS Lett*., 2000, 480, 2–16; Jungblut, et al., *Electrophoresis*, 1999, 20, 2100–10), expressed sequence tag (EST) sequencing (Celis, et al., *FEBS Lett*., 2000, 480, 2–16; Larsson, et al., *J. Biotechnol*., 2000, 80, 143–57), subtractive RNA fingerprinting (SuRF) (Fuchs, et al., *Anal. Biochem*., 2000, 286, 91–98; Larson, et al., *Cytometry*, 2000, 41, 203–208), subtractive cloning, differential display (DD) (Jurecic and Belmont, *Curr. Opin. Microbiol*., 2000, 3, 316–21), comparative genomic hybridization (Carulli, et al., *J. Cell Biochem. Suppl*., 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines; and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfonate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne $(—CH_2—)_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4.,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Interferon gamma receptor 2 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Interferon gamma receptor 2, enabling sandwich and other assays to easily be constructed to exploit this fact. Hybridization of the antisense oligonucleotides of the invention with a nucleic acid encoding Interferon gamma receptor 2 can be detected by means known in the art. Such means may include conjugation of an enzyme to the oligonucleotide, radiolabelling of the oligonucleotide or any other suitable detection means. Kits using such detection means for detecting the level of Interferon gamma receptor 2 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. patent application Ser. Nos. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun*., 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci*., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci*., 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A*., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem.*

*Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol*., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 *In: Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther*., 1992, 263, 25; Yamashita et al., *J. Pharm. Sci*., 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr*., 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel*., 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol*., 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev*., 1995, 5, 115–121; Takakura et al., *Antisense & Nucl. Acid Drug Dev*., 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxiten, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me—C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.249 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 ml., 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoetlhyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$—, 2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)-ethyl)]-5-methyl Uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P═O) oligonucleotides are synthesized on an automated DNA synthesizer (Applied Biosystems model 380B) using standard phosphoramidite chemistry with oxidation by iodine.

Phosphorothioates (P═S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O—Me]--[2'-deoxy]--[2'-O—Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]--[2'-deoxy]—[2'-O-(Methoxyethyl)] Chimeric Phosphorothioate Oligonucleotides

[2'-O-(2-methoxyethyl)]--[2'-deoxy]--[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl) Phosphodiester] Chimeric Oligonucleotides

[2'-O-(2-methoxyethyl phosphodiester]--[2'-deoxy phosphorothioate]--[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Interferon Gamma Receptor 2 Expression Antisense modulation of Interferon gamma receptor 2 expression can be assayed in a variety of ways known in the art. For example, Interferon gamma receptor 2 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of Interferon gamma receptor 2 can be quantitated in a variety of ways well known in the art, such as immunoprecipitation, Western blot analysis (immunoblotting), ELISA or fluorescence-activated cell sorting (FACS). Antibodies directed to Interferon gamma receptor 2 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Pro-*

*tocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Interferon Gamma Receptor 2 mRNA Levels

Quantitation of Interferon gamma receptor 2 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1× TAQMAN™ buffer A, 5.5 mM $MgCl_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human Interferon gamma receptor 2 were designed to hybridize to a human Interferon gamma receptor 2 sequence, using published sequence information (GenBank accession number NM_005534, incorporated herein as SEQ ID NO:3). For human Interferon gamma receptor 2 the PCR primers were:

forward primer: CAGCAGGCTTCCCAATGG (SEQ ID NO: 4)

reverse primer: GGAGGCCCGACAGTCACAT (SEQ ID NO: 5) and the

PCR probe was: FAM-TCAATGTCACTCTACGCCTTCGAGCTGA-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

forward primer: GAAGGTGAAGGTCGGAGTC (SEQ ID NO: 7)

reverse primer: GAAGATGGTGATGGGATTTC (SEQ ID NO: 8) and the

PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Interferon Gamma Receptor 2 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human Interferon gamma receptor 2, a human Interferon gamma receptor 2 specific probe was prepared by PCR using the forward primer CAGCAGGCTTCCCAATGG (SEQ ID NO: 4) and the reverse primer GGAGGCCCGACAGTCACAT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Interferon Gamma Receptor 2 Expression by Chimeric Phosphorothioate Oligonucleotides having 2'-MOE Wings and a Deoxy Gap In accordance with the present invention, a series of oligonucleotides were designed to target different regions of the human Interferon gamma receptor 2 RNA, using published sequences (GenBank accession number NM_005534, incorporated herein as SEQ ID NO: 3, GenBank accession number AI214335, incorporated herein as SEQ ID NO: 10, and genomic sequence representing residues 24001-78000 of GenBank accession number AP000045, incorporated herein as SEQ ID NO: 11). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-methylcytidines. The compounds were analyzed for their effect on human Interferon gamma receptor 2 mRNA levels by quantitative real-time PCR as described in other examples herein. Data are averages from two experiments. If present, "N.D." indicates "no data".

TABLE 1

Inhibition of human Interferon gamma receptor 2 mRNA levels by chimeric phosphorothicate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 142740 | 5'UTR | 3 | 96 | catattaagctttcaactct | 17 | 12 |
| 142741 | 5'UTR | 3 | 130 | agtcgaaatgtttgctttaa | 19 | 13 |
| 142742 | 5'UTR | 3 | 150 | attcgaggattcgccccttt | 22 | 14 |
| 142743 | 5'UTR | 3 | 161 | ttgatcgcacaattcgagga | 22 | 15 |
| 142744 | 5'UTR | 3 | 262 | cgatccttccggaagggccc | 4 | 16 |
| 142745 | 5'UTR | 3 | 337 | ggcctcccagagcgcggagc | 19 | 17 |
| 142746 | Coding | 3 | 741 | tcttcgggtgctgaggagcg | 55 | 18 |
| 142747 | Coding | 3 | 769 | aggacctgctctgcgttgta | 60 | 19 |
| 142748 | Coding | 3 | 786 | ccactggctcccaactcagg | 52 | 20 |
| 142749 | Coding | 3 | 818 | gtagacaacaggcctcgtgc | 39 | 21 |
| 142750 | Coding | 3 | 845 | actgtcggtgtatttaaact | 16 | 22 |
| 142751 | Coding | 3 | 864 | tgtcggccgtgaaccattta | 70 | 23 |
| 142752 | Coding | 3 | 885 | aattcacccctatggacatg | 48 | 24 |
| 142753 | Coding | 3 | 905 | tgttgctgtgatctgtgtac | 51 | 25 |
| 142754 | Coding | 3 | 911 | acactctgttgctgtgatct | 62 | 26 |
| 142755 | Coding | 3 | 917 | gaagtcacactctgttgctg | 76 | 27 |
| 142756 | Coding | 3 | 955 | aaatccattgggaagcctgc | 70 | 28 |
| 142757 | Coding | 3 | 975 | gaaggcgtagagtgacattg | 73 | 29 |
| 142758 | Coding | 3 | 991 | gctcccagctcagctcgaag | 91 | 30 |
| 142759 | Coding | 3 | 1000 | gaatggagtgctcccagctc | 81 | 31 |
| 142760 | Coding | 3 | 1013 | tgtcacccaggcagaatgga | 80 | 32 |
| 142761 | Coding | 3 | 1033 | tagtgttgaaaccaaggcat | 54 | 33 |
| 142762 | Coding | 3 | 1051 | ccgacagtcacattccgata | 60 | 34 |
| 142763 | Coding | 3 | 1073 | cacctcaatgttttctggag | 64 | 35 |
| 142764 | Coding | 3 | 1144 | aaggccgtggaggtatcagc | 66 | 36 |
| 142765 | Coding | 3 | 1180 | cctcctttttcccagtaatg | 37 | 37 |
| 142766 | Coding | 3 | 1201 | gggcctttgacctgttggat | 66 | 38 |
| 142767 | Coding | 3 | 1233 | agttatccaatgaaatggag | 47 | 39 |
| 142768 | Coding | 3 | 1253 | gtacactctggagggtttta | 67 | 40 |

TABLE 1-continued

Inhibition of human Interferon gamma receptor 2 mRNA levels by chimeric phosphorothicate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 142769 | Coding | 3 | 1268 | ctggacttgtaaacagtaca | 66 | 41 |
| 142770 | Coding | 3 | 1291 | cttttgttccaaagcagttg | 57 | 42 |
| 142771 | Coding | 3 | 1306 | actctaaagatgttactttt | 31 | 43 |
| 142772 | Coding | 3 | 1308 | cgactctaaagatgttactt | 8 | 44 |
| 142773 | Coding | 3 | 1316 | taaatgcccgactctaaaga | 49 | 45 |
| 142774 | Coding | 3 | 1321 | ttgcttaaatgcccgactct | 39 | 46 |
| 142775 | Coding | 3 | 1341 | ttgtttcgtagcaagatatg | 45 | 47 |
| 142776 | Coding | 3 | 1361 | ctcagtggaggcatctgcca | 67 | 48 |
| 142777 | Coding | 3 | 1370 | ttgctgaagctcagtggagg | 57 | 49 |
| 142778 | Coding | 3 | 1399 | gaaaatgttcccacggagat | 19 | 50 |
| 142779 | Coding | 3 | 1409 | cgacagcaacgaaaatgttc | 49 | 51 |
| 142780 | Coding | 3 | 1426 | caggctcctgccagcaccga | 67 | 52 |
| 142781 | Coding | 3 | 1496 | taatgggatgcttggtggag | 28 | 53 |
| 142782 | Coding | 3 | 1514 | taaatactcttctatctgta | 39 | 54 |
| 142783 | Coding | 3 | 1540 | tctaagatgggctgagttgg | 41 | 55 |
| 142784 | Coding | 3 | 1575 | cgtcatcctttggtgagctg | 59 | 56 |
| 142785 | Coding | 3 | 1595 | aatggacacagagtcccaga | 59 | 57 |
| 142786 | Coding | 3 | 1601 | cgagataatggacacagagt | 23 | 58 |
| 142787 | Stop Codon | 3 | 1654 | catgctttggttcaaagcgt | 50 | 59 |
| 142788 | 3'UTR | 3 | 1667 | agtgggctaggcccatgctt | 36 | 60 |
| 142789 | 3'UTR | 3 | 1682 | ctcttccagggagccagtgg | 42 | 61 |
| 142790 | 3'UTR | 3 | 1689 | gcttgatctcttccagggag | 42 | 62 |
| 142791 | 3'UTR | 3 | 1707 | actctagcagctccgatggc | 59 | 63 |
| 142792 | 3'UTR | 3 | 1749 | ggcagcaaaagggaatactg | 32 | 64 |
| 142793 | 3'UTR | 3 | 1780 | ctctcatgtctgcagggaca | 52 | 65 |

TABLE 1-continued

Inhibition of human Interferon gamma receptor 2 mRNA levels by chimeric phosphorothicate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 142794 | 3'UTR | 3 | 1804 | tgtcacccccatgagacctg | 50 | 66 |
| 142795 | 3'UTR | 3 | 1839 | ttttgaaaattctttaagaa | 5 | 67 |
| 142796 | 3'UTR | 3 | 1921 | caagcaattacatgcctttt | 56 | 68 |
| 142797 | 3'UTR | 3 | 1954 | agtatcagagatgtgtcata | 57 | 69 |
| 142798 | 3'UTR | 3 | 1987 | ttctgactgctcagcccaac | 52 | 70 |
| 142799 | 3'UTR | 3 | 2006 | tcaagacgacgaccaggtct | 48 | 71 |
| 142800 | 3'UTR | 3 | 2012 | ccaaagtcaagacgacgacc | 40 | 72 |
| 142801 | 3'UTR | 3 | 2075 | gccactcagtgtccctcgct | 48 | 73 |
| 142802 | 3'UTR | 3 | 2087 | tgtacatgaagggccactca | 55 | 74 |
| 142803 | 3'UTR | 3 | 2093 | catggatgtacatgaagggc | 33 | 75 |
| 142804 | 3'UTR | 3 | 2109 | ttttaagccagcacaccatg | 48 | 76 |
| 142805 | 3'UTR | 3 | 2120 | gattaattacattttaagcc | 20 | 77 |
| 142806 | 3'UTR | 3 | 2130 | atatttacaagattaattac | 21 | 78 |
| 142807 | Exon | 10 | 184 | tcactgggccctttctaact | 28 | 79 |
| 142808 | Exon | 10 | 190 | cctccttcactgggcccttt | 0 | 80 |
| 142809 | Exon | 10 | 264 | tagaaatgctggaagtttct | 13 | 81 |
| 142810 | Exon | 10 | 293 | gccggctccagggcaaaccc | 20 | 82 |
| 142811 | Intron 1 | 11 | 7996 | ttgggtgacagagagagact | 5 | 83 |
| 142812 | Intron 1 | 11 | 8566 | aagttattctaattggatgg | 39 | 84 |
| 142813 | Intron 2 | 11 | 16852 | ttcttagagtgtagaacaac | 12 | 85 |
| 142814 | Intron 3 | 11 | 20075 | gaggaacaaatgtaggaact | 52 | 86 |
| 142815 | Intron 3 | 11 | 21224 | cctgggcgacagtgcaagac | 22 | 87 |
| 142816 | Intron 3 | 11 | 22073 | gctctgtcacccaggctgat | 39 | 88 |
| 142817 | Intron | 11 | 24417 | tctcttgcatcagcctctca | 28 | 89 |

As shown in Table 1, SEQ ID NOs 18, 19, 20, 23, 24, 25, 26, 27, 28, 29, 30, 31, 32, 33, 34, 35, 36, 38, 39, 40, 41, 42, 45, 47, 48, 49, 51, 52, 55, 56, 57, 59, 61, 62, 63, 65, 66, 68, 69, 70, 71, 72, 73, 74, 76 and 86 demonstrated at least 40% inhibition of human Interferon gamma receptor 2 expression in this assay and are therefore preferred. The target sites to which these preferred sequences are complementary are herein referred to as "active sites" and are therefore preferred sites for targeting by compounds of the present invention.

Example 16

Western Blot Analysis of Interferon Gamma Receptor 2 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Interferon gamma receptor 2 is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 50 nucleobases in length targeted to a region consisting of nucleobases 1000 through 1092 of a nucleic acid molecule encoding human Interferon gamma receptor 2 (SEQ ID NO. 3), wherein said compound is an antisense oligonucleotide which comprises at least one modified internucleoside linkage and wherein said compound specifically hybridizes with said region and inhibits the expression of human Interferon gamma receptor 2.

2. The compound of claim 1 wherein the modified internucleoside linkage is a phosphorothioate linkage.

3. The compound of claim 1 wherein the antisense oligonucleotide comprises at least one modified sugar moiety.

4. The compound of claim 3 wherein the modified sugar moiety is a 2'-O-methoxyethyl sugar moiety.

5. The compound of claim 1 wherein the antisense oligonucleotide comprises at least one modified nucleobase.

6. The compound of claim 5 wherein the modified nucleobase is a 5-methylcytosine.

7. The compound of claim 1 wherein the antisense oligonucleotide is a chimeric oligonucleotide.

8. A composition comprising the compound of claim 1 and a pharmaceutically acceptable carrier or diluent.

9. The composition of claim 8 further comprising a colloidal dispersion system.

* * * * *